(12) United States Patent
Sengupta et al.

(10) Patent No.: US 8,754,206 B2
(45) Date of Patent: Jun. 17, 2014

(54) METAL (III) COMPLEX OF BIURET-AMIDE BASED MACROCYCLIC LIGAND AS GREEN OXIDATION CATALYST

(75) Inventors: Sayam Sengupta, Pune (IN); Chakadola Panda, Pune (IN); Munmun Ghosh, Pune (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/478,957

(22) Filed: May 23, 2012

(65) Prior Publication Data

US 2012/0329680 A1 Dec. 27, 2012

(30) Foreign Application Priority Data

Jun. 21, 2011 (IN) .......................... 1747/DEL/2011

(51) Int. Cl.
*C07F 5/00* (2006.01)
*C07F 15/02* (2006.01)
*C07F 15/04* (2006.01)
*C07F 15/06* (2006.01)
*C40B 50/08* (2006.01)

(52) U.S. Cl.
USPC ............................................. 540/452; 532/1

(58) Field of Classification Search
CPC .......... C07F 15/02; C07F 15/04; C07F 15/06; C07F 11/00; C07F 5/00
USPC ............................................. 540/452; 532/1
See application file for complete search history.

(56) References Cited

U.S. PATENT DOCUMENTS

| 6,051,704 A | * | 4/2000 | Gordon-Wylie et al. ..... 540/465 |
| 7,060,818 B2 | * | 6/2006 | Horwitz et al. ............... 540/450 |
| 2011/0094043 A1 | | 4/2011 | Ghosh et al. |

FOREIGN PATENT DOCUMENTS

WO    WO 2011137190 A1 * 11/2011

OTHER PUBLICATIONS

Pera-Titus et al., Degradation of Chlorophenols by Means of Advanced Oxidation Processes: A General Review, Applied Catalysis B: Environmental, 2004, 47, 219-256.*
Collins, T., TAML Oxidant Activators: A New Approach to the Activation of Hydrogen Peroxide for Environmentally Significant Problems, Acc. Chem. Res., 2002, 35, 782-790.*
Panda et al., Fe(III) Complex of Biuret-Amide Based Macrocyclic Ligand as Peroxidase Enzyme Mimic, Chem. Commun., Jun. 14, 2011, 47, 8016-8018.*
Malvi et al.; One Pot Glucose Detection by [FeIII(biuret-amide)] Immobilized on Mesoporus Silica Nanoparticles: An Efficient HRP Mimic; Chem. Commun., 2012, 48, 5289-5291.*
Ganai et al.; Synthesis of Functional Hybred Silica Scaffolds With Controllable Hierarchical Porosity by Dynamic Templating; Chem. Commun., 2012, 48, 5292-5294.*
Ghosh, et al.; "Catalase-Peroxidase Activity of Iron(III)-TAML Activators of Hydrogen Peroxide"; J. Am. Chem. Soc. 2008, 130, 15116-15126.
Horner, et al.; "Coordination Complexes of New Acyclic and Macrocyclic Ligands"; 1998; 3 pages.
Nasman, et al.; "Nineteen-membered pentaazamacrocyclic complexes bearing tetraamide groups"; Transition Metal Chemistry, vol. 22, No. 3, 1997, pp. 273-276(4).
Kaizer, et al; "Nonheme FeIVo Complexes That Can Oxidize the C—H Bonds of Cyclohexane at Room Temperature" J. Am. Chem. Soc. 2004, 126, 472.
Nasman; "Tetraamide Macrocyclic Complexes of Some Transition Metal Ions"; Journal of Al Azhar University—Gaza (Natural Sciences), (2007), vol. 9, p. 53-59.
Shakir, et al.; "Tetraamide macrocyclic complexes of transition metals with ligands derived from hydrazine"; Transition Metal Chemistry vol. 22, No. 2 (1997), 189-192.
Filipe Tiago de Oliveira, Arani Chanda, Deboshri Banerjee, Xiaopeng Shan, Sujit Mondal, Lawrence Que Jr., Emile L. Bominaar, Eckard Münck, Terrence J. Collins; "Chemical and Spectroscopic Evidence for an FeV-Oxo Complex"; Science, 315, 9, 835-838.
F. Weigend, R. Ahlrichs, "A fully direct RI-HF algorithm Implementation, optimised auxiliary basis sets, demonstration of accuracy and efficiency"; Physical Chemistry Chemical Physics; 2005, 7, 3297-3305.
Stevens, P. J.; Devlin, F. J.; Chablowski, C. F.; Frisch, M. J.; "Ab Initio Calculation of Vibrational Absorption and Circular Dichroism Spectra Using Density Functional Force Fields" J. Phys. Chem. 1994, 80, 11623.
K. Eichkorn, O. Treutler, H. Oehm, M. Haeser, R. Ahlrichs, "Auxiliary basis sets to approximate Coulomb potentials"; Chem. Phys. Lett. 1995, 240, 283-290.
F. Weigend, R. Ahlrichs, "Balanced basis sets of split valence, triple zeta valence and triple zeta valence and quadruple zeta valence for H to Rn Desiogn assessment of accuracy"; Physical Chemistry Chemical Physics 2005, 7, 3297-3305.
Filipe Tiago de Oliveira, Arani Chanda, Deboshri Banerjee, Xiaopeng Shan, Sujit Mondal, Lawrence Que Jr., Emile L. Bominaar, Eckard Münck, Terrence J. Collins; "Chemical and Spectroscopic Evidence for an FeV-Oxo Complex"; Science, 315, 9, 835-838, 2007.

(Continued)

*Primary Examiner* — Maria Leavitt
*Assistant Examiner* — Amy M Bunker
(74) *Attorney, Agent, or Firm* — St. Onge Steward Johnston & Reens LLC

(57) ABSTRACT

The present invention discloses metal (III) complex of a biuret-amide based macrocyclic ligand as green catalysts that exhibit both excellent reactivity for the activation of $H_2O_2$ and high stability at low pH and high ionic strength. The invention also provides macrocyclic biuret amide based ligand for designing of functional peroxidase mimics. Further, the present invention discloses synthesis of said metal (III) complex of a biuret-amide based macrocyclic ligand.

13 Claims, 14 Drawing Sheets

(56) References Cited

OTHER PUBLICATIONS

Becke, A. D.; "Density-functional thermochemistry. III. The role of exact exchange"; J. Chem. Phys. 1993, 98, 5648-5652.

R. Ahlrichs, M. Baer, M. Haeser, H. Horn, C. Koelmel, "Electronic Structure Calculations on Workstation Computers: The Program System Turbomole"; Chem. Phys. Lett. 1989, 162, 165-169.

M. Sierka, A. Hogekamp, R. Ahlrichs, "Fast evaluation of the Coulomb potential for electron densities using multipole accelerated resolution of identity approximation"; J. Chem. Phys. 2003, 118, 9136-9148.

A. Schaefer, H. Horn, R. Ahlrichs, "Fully optimized contracted Gaussian basis sets for atoms Li to Kr"; Journal of Chemical Physics 1992, 97, 2571-2577.

Schaefer, C. Huber, R. Ahlrichs, "Fully optimized contracted Gaussian basis sets of triple zeta valence quality for atoms Li to Kr"; Journal of Chemical Physics 1994, 100, 5829-5835.

J. P. Perdew, K. Burke, M. Ernzerhof, "Generalized Gradient Approximation Made Simple"; Phys. Rev. Lett. 1996, 77, 3865.

Soumen Kundu, Jasper Van Kirk Thompson, Alexander D. Ryabov, and Terrence J. Collins; "On the Reactivity of Mononuclear Iron(V)oxo Complexes"; J. Am. Chem. Soc., 2011, 133 (46), 18546-18549.

Hariharan, P. C.; Pople, "The Effect of d-Functions on Molecular Orbital Energies for Hydrocarbons"; J. A. Chem. Phys. Lett. 1972, 16, 217-219.

* cited by examiner

METAL (III) COMPLEX OF BIURET-AMIDE BASED MACROCYCLIC LIGAND AS GREEN OXIDATION CATALYST

FIELD OF THE INVENTION

The present invention relates to metal (III) complex of a biuret-amide based macrocyclic ligand as green catalysts that exhibit both excellent reactivity for the activation of $H_2O_2$ and high stability at low pH and high ionic strength. The invention also relates to macrocyclic biuret amide based ligand for designing of functional peroxidase mimics that acts as an oxidation catalyst. The present invention further relates to the synthesis of said metal complex of a biuret-amide based macrocyclic ligand.

BACKGROUND AND PRIOR ART OF THE INVENTION

In present world adequate amount of clean water supply is a challenging task due to contamination of surface water as well as ground water by synthetic chemicals like polychlorophenot, nitrophenols, thiophosphate pesticides, herbicides, textile azodyes and dibenzothiophenes which enter into environment from industrial effluents, domestic sewage and agriculture run off. To reduce the impact of environmental release of those pollutants and to increase water reusability oxidation chemistry plays a crucial role.

Catalyst fate is an important issue in both the economic and environmental performances of any new technology. However, designing metal complexes that activate $H_2O_2O_2$ or $O_2$ but are themselves inert to oxidation is the key to the synthesis of efficient transition metal oxidation catalysts. An approach pursued by researchers to achieve this goal has been to mimic enzymes that function as oxidation catalysts. Nature has evolved enzymes that are very efficient as oxidation catalysts. These include cytochrome P450 and peroxidases, enzymes that use an iron (IV) oxoporphyrin radical cation intermediate to catalyze the oxidation of various organic substrates selectively and efficiently. Though the enzymes that activate "Green" oxidants like $O_2$ or $H_2O_2$ in aerobic biochemistry exhibit remarkable activity and selectivity, however, limits their technological applicability due to high costs, limited availability and less activity at extreme pH limit and ionic strength.

Macrocyclic ligands with various donor atoms are very important to stabilize metals with high valent oxidation states. Such macrocyclic complexes play a significant role in mimicking either structure and/or functions of several metallo enzymes, especially enzymes which use hydrogen peroxides or oxygen for their activity, Fe (III) complexes based on a class of tetraamidemacrocyclic ligands (Fe-TAML's) developed by Collins et. al. have several attributes that render them to be excellent functional mimics of peroxidases. In recent years various synthetic methods for TAML ligand has been reported.

References may be made to an article entitled 'Catalase-Peroxidase Activity of Iron(III)-TAML Activators of Hydrogen Peroxide' by Anindya Ghosh, Douglas A. Mitchell et. al in J. AM. CHEM. SOC. 2008, 130, 15116-15126 disclose FeIII-TAML Activators of Hydrogen Peroxide oxidation of a wide spectrum of targets including toxic polychlorophenols, thiophosphate pesticides and nitrophenols, azo dyes, dibenzothiophenes, an anthrax surrogate, and natural and synthetic estrogens.

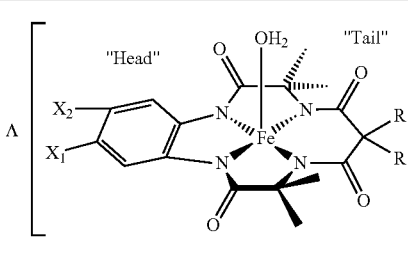

| | $X_1$ | $X_2$ | R |
|---|---|---|---|
| a | H | H | $CH_3$ |
| b | $NO_2$ | H | $CH_3$ |
| c | H | H | F |
| d | Cl | Cl | F |
| | MeOOC | H | $CH_3$ |
| | Cl | Cl | $CH_3$ |
| | $CH_3$ | H | $CH_3$ |
| | $CH_3$ | $CH_3$ | $CH_3$ |
| | COOH | H | $CH_3$ |

References may be made to U.S. Pat. No. 7,060,818 which relate to macrocyclic tetramido compounds and to a process for metal insertion. The complex is given below:

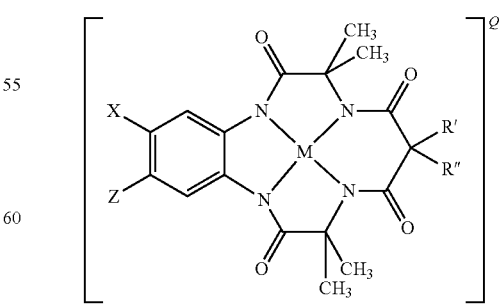

The tetra amido macrocyclic ligand is prepared by the process given below:

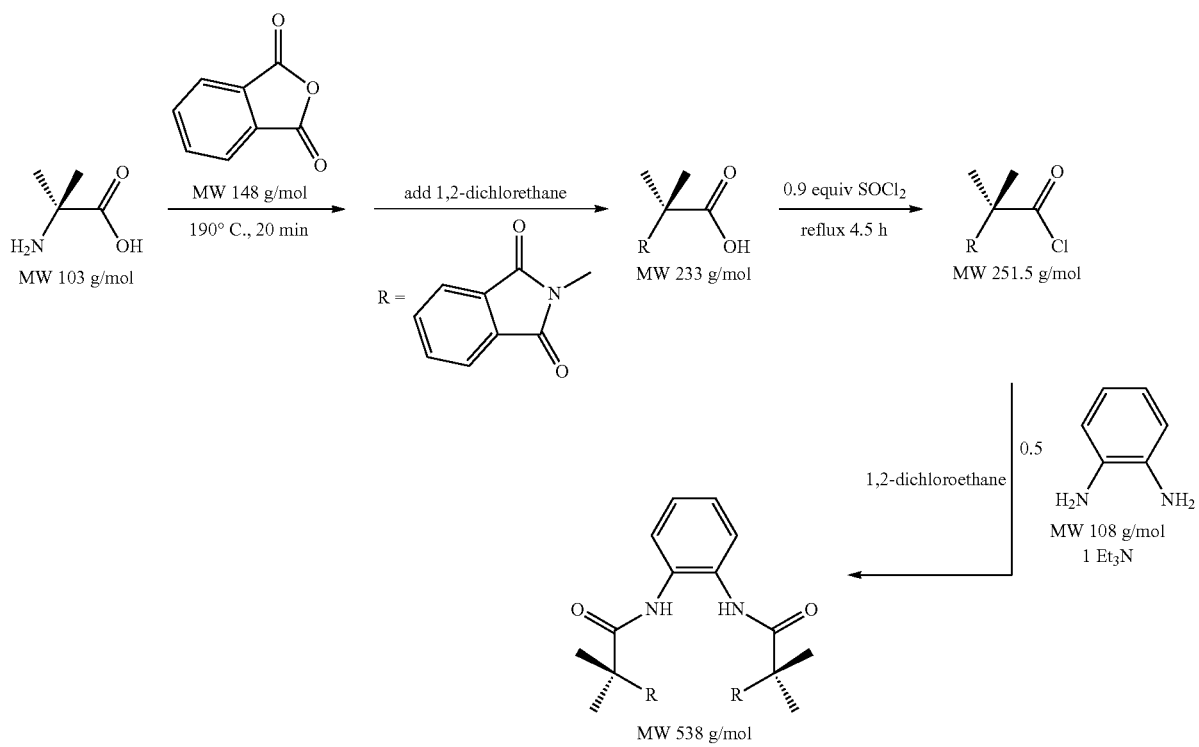

The diamide diamine intermediate is reacted with an activating diacid to form the macrocyclic tetramido compound having at least 11 atoms forming the macrocycle. Further, the said patent discloses the formation of LiFeB* as given below:

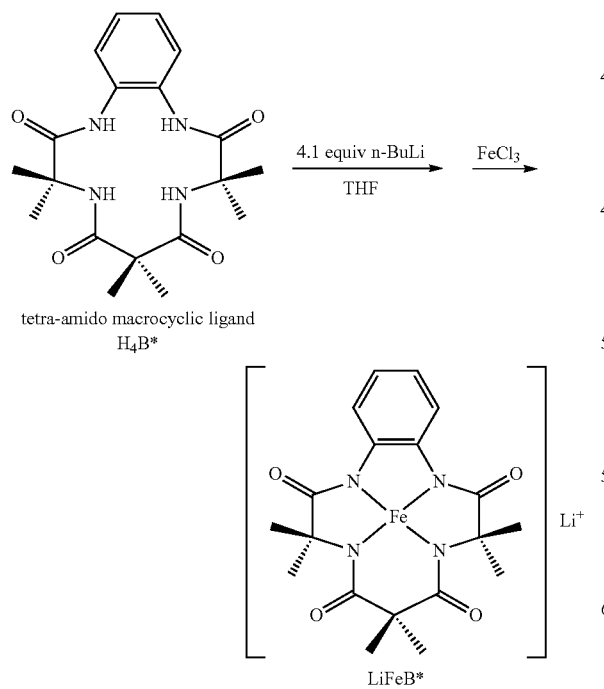

References may be made to an article titled "Nineteen-membered pentaazamacrocyclic complexes bearing tetraamide groups" by Nasman O. S. M. Baraka R. M et. al in Transition Metal Chemistry, Volume 22, Number 3, 1997, pp. 273-276(4) disclose a series of CoII, NiII, CuII and ZnII complexes incorporating pentaazamacrocyclic ligands via the template condensation of o-aminobenzoic acid with succinic or phthalic acids in the presence of diethylenetriamine. An article titled 'Tetraamide Macrocyclic Complexes of Some Transition Metal Ions' by Omar S. M. Nasman in Journal of Al Azhar University-Gaza (Natural Sciences), (2007), Vol. 9, page: 53-59 disclose a series of tetraazamacrocyclic complexes prepared by a process as shown in scheme below:

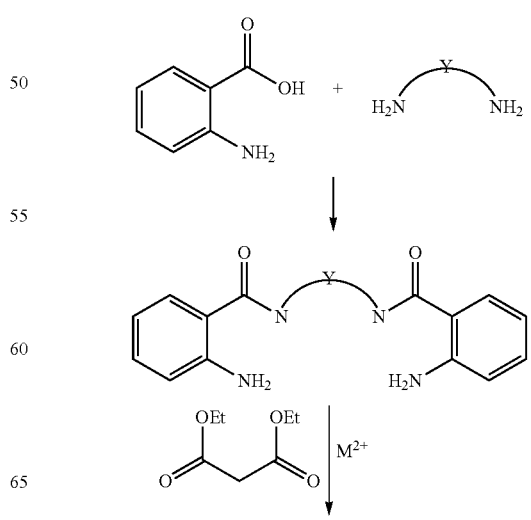

-continued

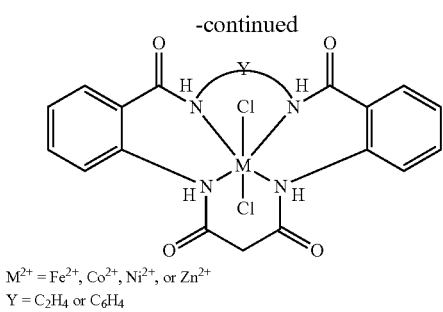

$M^{2+} = Fe^{2+}, Co^{2+}, Ni^{2+},$ or $Zn^{2+}$
$Y = C_2H_4$ or $C_6H_4$

A series of tetraazamacrocyclic complexes bearing tetraamide groups is derived from o-aminobenzoic acid, with ethylene diamine or o-phenylene diamine and diethyl malonate in the presence of transition metal ions as templates. These complexes may be useful for investigation of metal containing—biological molecules such as metalloenzymes, and their catalytic activity for industry.

References may be made to patent application US201109043, which claims a process for synthesizing a tetradentate amido macrocyclic ligand (1), comprising:

(a) protecting one of the amine groups of o-phenylene diamine with a tert-butyloxy carbonyl group (BOC);

(b) reacting the product of step (a) with dimethyl malonyl chloride in the presence of triethylamine;

(c) reacting the product of step (b) with trifluoroacetic acid to remove the protecting BOC group; and (d) reacting the product of step (c) with oxalyl chloride in the presence of triethylamine to produce a tetradentate amido macrocycle ligand (1).

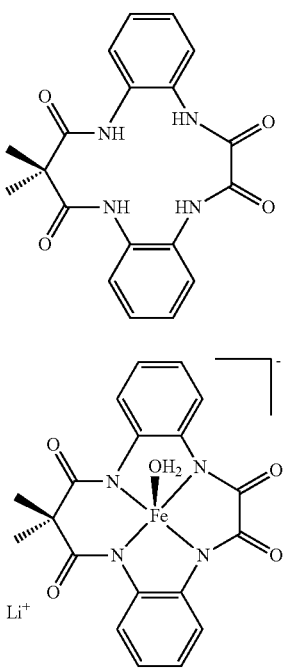

Ligand (1) was further deprotonated using a strong base, n-butyllithium, and reacted with ferrous chloride in dry tetrahydrofuran and exposing the resulting mixture to air to obtain Fe complex (2). The synthesized Fe-complex in said patent is used as an activator of $H_2O_2$ in various oxidation chemistries.

References may be made to thesis titled 'Coordination Complexes of New Acyclic and Macrocyclic Ligands' by Horner, Stephen Thomas deals with the design and synthesis of a series of acyclic and macrocyclic ligands containing pyridine and amide groups. It is disclosed in the abstract the complexes of acyclic ligand designated $H_2LMe$ which and has methyl groups attached to the pendant pyridine groups. An anionic iron complex with two deprotonated ligands coordinated around the metal center is synthesized and structurally characterized as $[Et_4N][Fe(LMe)_2]$. A related tetraamide extended ligand with ferrocenyl groups is also disclosed which is synthesized by the reaction of Fe(CoCl) with $H_2O_2$. It is further disclosed that macrocycles are formed by double Michael addition of amines to the vinyl groups of ligand. In particular, reaction with n-butylamine gave the macrocycle H4LnBu, and reaction with ethylenediamine gave H4Len in high yield. Cobalt complexes of both these macrocycles and the acyclic precursor, H4LacrA, are also studied. The complex formed with the acyclic ligand contain two ligands coordinated to the cobalt center via the pendant rather than the headgroup amides, resulting in a square-planar coordination geometry around the cobalt center.

References may be made to an abstract in an article titled 'Tetraamide macrocyclic complexes of transition metals with ligands derived from hydrazine' by Mohammad Shakir, Khan S. Islam, Transition Metal Chemistry Volume 22, Number 2 (1997), 189-192 disclose succinic acid or phthalic acid reaction with hydrazine hydrate and formaldehyde in the presence of metal ions to give the macrocyclic complexes $[ML_1Cl_2]$ or $[ML_2Cl_2][M=FeII, CoII, NiII, CuII$ and $ZnII]$. The coordination of amide groups through nitrogen and the overall geometry of the complexes have been assigned on data obtained from elemental analyses and all the complexes exhibit an octahedral geometry, except copper which is square planar, where the amide group coordinates through nitrogen, and are air stable. $[ML_1Cl_2]$ disclosed relates to dichloro(6,9,15,18-tetraone-1,2,4,5,10,11,13,14-octaazacyclooctadecane) metal (II); $[ML_2Cl_2]$ is dichloro(6,9,15,18-tetraone-7,8,16,17 dibenzol1,2,4,5,10,11,13,14 octaazacyclooctadecane) metal (II) where M is Fe, Co, Ni, Zn.

TAML (tetraamido macrocyclic ligand) catalyst is very much effective in nanomolar to low micromolar concentrations in aqueous media with turnover frequencies thousands per minute that are similar to native peroxidases. The very high turnover number observed for this class of catalysts has been shown the robustness of the tetraamido macrocyclic ligand framework which makes these Fe(III) complexes resistant to oxidative degradation. They have been used to perform various oxidations in water using $H_2O_2$ and can be used for the degradation of various environmental pollutants. But the major problem of this catalyst is it loses activity below pH 4 due to acid catalyzed demetalation.

The stability and reactivity of Fe-TAML's are best controlled by modulating the σ-donor ability of the deprotonated amide nitrogen atoms in the 6-membered ring. Replacement of the —$CMe_2$ by the corresponding electron withdrawing —$CF_2$ in the malonyl fragment of the 6-membered ring shows very positive effects on acid stability and reaction rates. But fluorinated —$CF_2$ unit in the catalyst framework renders its usage unsuitable for water treatment applications and is not eco-friendly.

Therefore optimizing environmental clash and developing low molecular weight protein free inorganic 'Green catalyst' that competes catalytically while showing robustness in extreme acidic and basic environment remains a challenge to the scientific community.

In the above context, the present inventor has sought to develop environmentally friendly macrocylic ligands and its metal complex that can lead to new generation of peroxidase mimics and function as oxidation catalyst. It is the object of the invention to provide metal complexes of oxidatively robust frameworks with selected macrocyclic rigid ligands, and to develop a simple high yielding process of preparation thereof, which have attributes better than the $CF_2$ functionalized Fe-TAML.

Further, it has been shown that high-valent iron-oxo species are the key reactive intermediates in the catalytic dioxygen activation by heme and non-heme iron enzymes. These reactive intermediates either follow an oxygen atom transfer or electron transfer for the oxidation of myriads of substrates. Hence it has dragged a huge interest in designing both heme and non-heme iron complexes that would mimic the native enzymes where a high valent Fe-oxo species is achievable upon oxidation. A ligand system that is resistant to oxidation and helps stabilizing the high valent Fe-oxo species injecting more electron density is highly desired. $Fe^{IV}$-oxo species has already been synthesized and well characterized by spectroscopy and x-ray crystal structure [Jo'zsef Kaizer, Eric J. Klinker, Na Young Oh, Jan-Uwe Rohde, Woon Ju Song, Audria Stubna, Jinheung Kim, Eckard Munck, Wonwoo Nam, and Lawrence Que, Jr; J. Am. Chem. Soc. 2004, 126, 472.]. These species are stable at ambient temperature for a long time period and also able to oxidize unactivated C—H bonds like cyclohexane. However, a $Fe^{V}$-oxo species is believed to be more oxidizing in nature than $Fe^{IV}$-oxo species, and hence efforts have been made in making the same. In 2007 Collins and co-workers have trapped $Fe^{V}$-oxo species from [$Fe^{III}$-TAML] that is only stable at −40° C. and used for the oxidation of organic sulfide to sulfoxide [Filipe Tiago de Oliveira, Arani Chanda, Deboshri Banerjee, Xiaopeng Shan, Sujit Mondal, Lawrence Que Jr., Emile L. Bondmar, Eckard Münck, Terrence J. Collins; Science, 315, 9, 835; Soumen Kundu, Jasper Van Kirk Thompson, Alexander D. Ryabov, and Terrence J. Collins; J. Am. Chem. Soc., 2011, 133 (46), 18546]. However organic transformations could not be achieved at this temperature without ease.

OBJECTIVES OF THE INVENTION

Main objective of the present invention is to provide biocompatible metal (III) complex of a biuret-amide based macrocyclic ligand that exhibits both excellent reactivity for the activation of $H_2O_2$ and high stability at low pH and high ionic strength.

Another object of the present invention is to provide deprotonated Me-substituted biurets that can be excellent ligands for designing of functional peroxidase mimics acting as green oxidation catalyst.

SUMMARY OF THE INVENTION

Accordingly, present invention provides a biocompatible metal (III) complex of a biuret-amide based macrocyclic ligand of Formula (X), $$[M^{III}L_1] \cdot P$$ Formula X wherein
'M' is selected from group of elements that exhibit +3 oxidation states such as transition elements selected from the group consisting of Cr, Mn, Fe, Cu, Ni or Co; group in elements, inner transition elements such as lanthanides; L1 is a biuret-amide based macrocyclic ligand;

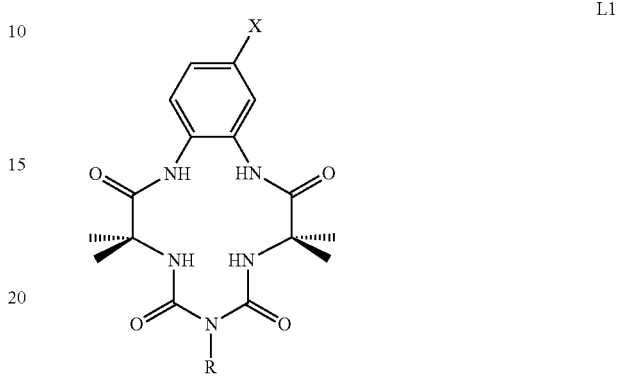

L1 wherein X=hydrogen or electron withdrawing groups selected from the group consisting of —$NO_2$, —COOH, —COO or —CN;

R=C1-C3 alkyl or phenyl which may be optionally substituted;

P represent a cation selected from $Li^+$ or $Et_4N^+$.

In an embodiment of the present invention, biocompatible metal (III) complex, wherein Fe (III) complex of a biuret-amide based macrocyclic ligand is represented by:

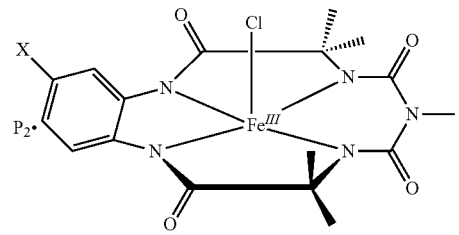

Formula 1 wherein X=hydrogen or electron withdrawing groups selected from the group consisting of —$NO_2$, —COOH, —COOR, —COO or —CN; P represent a cation selected from $Li^+$ or $Et_4N^+$ and representative compounds of formula 1 comprising:

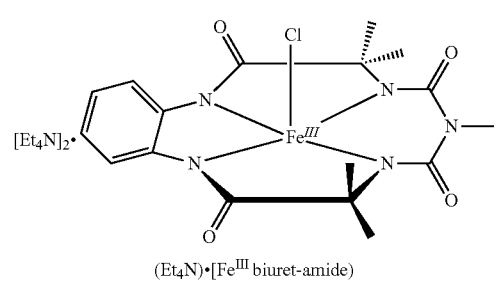

$(Et_4N) \cdot [Fe^{III}$ biuret-amide$]$

Tetraethyl ammonium 3,3,6,9,9-pentamethyl-1,4,8,
11-tetrahydro-1H-benzo[i][1,4,6,8,11]pentaazacyclo-
tridecine-2,5,7,10(6H,11H)-tetraone ferrate (1A)

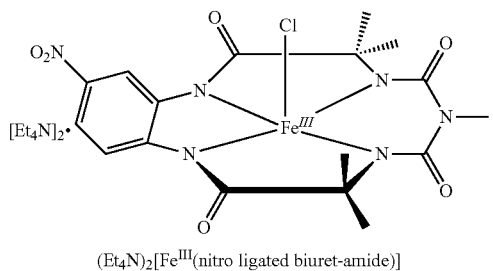

($Et_4N)_2$[$Fe^{III}$(nitro ligated biuret-amide)]

Tetraethyl ammonium 3,3,6,9,9-pentamethyl-13-
nitro-1,4,8,11-tetrahydro-1H benzo[i][1,4,6,8,11]
pentaazacyclotridecine-2,5,7,10(6H,11H)-tetraone
ferrate (1B)

In another embodiment of the present invention, macrocyclic biuret amide based ligand L1 for designing of functional peroxidase mimics represented by following compounds:

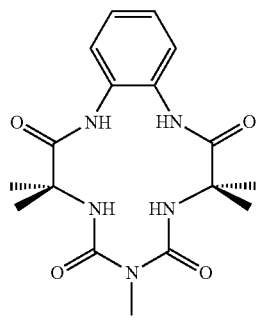

L1a

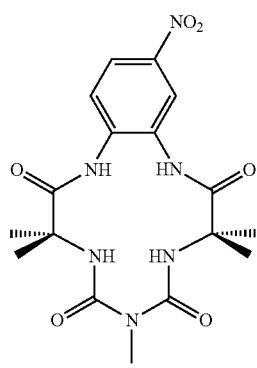

L1b

In yet another embodiment of the present invention, the biocompatible metal (III) complex of a biuret-amide based macrocyclic ligand of Formula X are useful for $H_2O_2$ oxidation of a wide spectrum of targets selected from the group consisting of toxic polychlorophenols, thiophosphate pesticides and nitrophenols, azo dyes, dibenzothiophenes, an anthrax surrogate, and natural and synthetic estrogens, in effluent bleaching, in small molecule synthesis by oxidation (e.g. N-oxides, epoxides, aldehydes), and as functioning analogues of catalase-peroxidase enzymes.

In yet another embodiment of the present invention, the biocompatible metal (III) complex of a biuret-amide based macrocyclic ligand of Formula (X), wherein the said metal complex exhibits excellent reactivity for the activation of $H_2O_2$, high stability at low pH and high ionic strength. In yet another embodiment of the present invention, simple high yielding synthesis of library of biocompatible transition metal (III) complex based on a macrocyclic biuret amide ligand of formula X comprising the steps of;

a. mixing diamine (1) in Tetrahydrofurane (THF) and base to obtain a mixture;

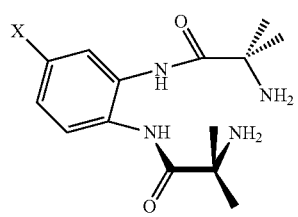

1 wherein X=hydrogen or electron withdrawing groups selected from the group consisting of —$NO_2$, —COOH, —COOR, —COCl or —CN;

b. adding N,N-dichloroformyl(aryl/alkylamine) (2) dissolved in dry THF in the mixture as obtained in step (a) at 0° C. under nitrogen for period in the range of 50 to 70 minutes to obtain a solution;

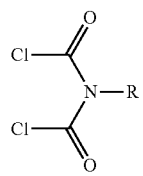

2

Wherein R=C1-C3 alkyl or phenyl which may be optionally substituted;

c. allowing the solution as obtained in step (b) to warm to temperature in the range of 25 to 35° C., stirring for 11 to 13 hours to obtain macrocylic ligand of Formula L1;

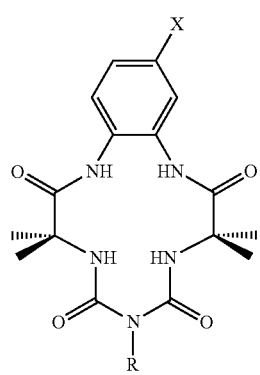

L1 wherein X=hydrogen or electron withdrawing groups selected from the group consisting of —$NO_2$, —COOH, —COOR, —COOl or —CN; R=C1-C3 alkyl or phenyl which may be optionally substituted;

d. inserting metal (III) using metal precursor into the biuret-amide ligand of Formula L1 in presence of a base and non-polar solvent followed by addition of a cationic salt by a process known in the art to Obtain biocompatible transition metal (III) complex based on a macrocyclic biuret amide ligand of formula X.

In yet another embodiment of the present invention, base used in step (a) is selected from diethylamine or triethylamine.

In yet another embodiment of the present invention, metal precursor used in step (d) is selected from group of elements that exhibit +3 oxidation states such as transition elements selected from the group consisting of Cr, Mn, Fe, Cu, Ni or Co; group III elements, inner transition elements such as lanthanides.

In yet another embodiment of the present invention, cation used in step (d) is selected from [Et$_4$N]$^+$ or Li$^+$.

In yet another embodiment of the present invention, the simple high yielding synthesis of library of biocompatible Fe (III) complex based on a macrocyclic biuret amide ligand comprising the steps of;
  a. cyclizing diamine (1) with N,N-dichloroformyl(aryl/alkyl)amine (2) dissolved in dry THF, base and chloroform at 0° C. under nitrogen, allowing to warm at temperature in the range of 25 to 35° C., stirring for about 12 hours to obtain macrocyclic ligand of Formula L1;
  b. inserting Fe (III) chloride into the biuret-amide ligand (L1a) using FeCl$_2$ in presence of a base n-butyl lithium and non-polar solvent followed by addition of Et4N$^+$ by a process known in the art to obtain compound of formula 1.

BRIEF DESCRIPTION OF DRAWINGS

FIG. 26 depicts $^1$H NMR of L1a.

DETAILED DESCRIPTION OF THE INVENTION

Figure 1:
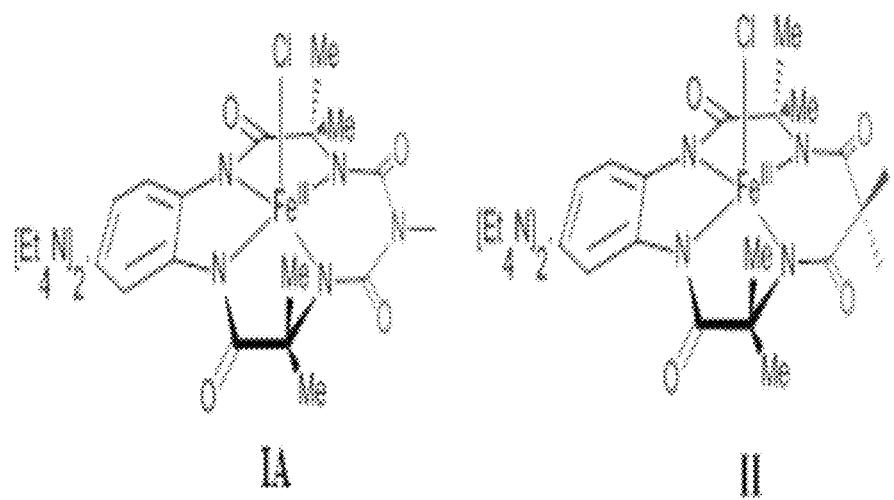
FIG. 1 depicts Molecular structure of (Et$_4$N)$_2$[Fe$^{III}$(biuret-amide)] (IA) and (Et$_4$N)$_2$[Fe$^{III}$(Cl)B*](III)

The compounds 'B*' and 'II' used alternately in the specification mean and refer to Fe(III) complex of TAML (tetraamido macrocyclic ligand) reported by Collins group.

The replacement of —CMe$_2$ of Fe-TAML by the corresponding electron withdrawing —CF$_2$ in the malonyl fragment as described above though shows very positive effects on acid stability and reaction rates, however the problem related with not so ecofriendly —CF$_2$ group limits its use in green oxidation catalysts.

Further, though deprotonated amide and urea ligands have been used to design H$_2$O$_2$ activating complexes, there are no reports of active oxidation catalysts synthesized using chelating biuret groups as ligands. Copper, nickel and cobalt complexes have been made of acyclic biuret ligands, but their applications have been limited to the study of their structural and spectroscopic properties.

In view of the foregoing, the present invention provides metal complex of a biuret-amide based macrocyclic ligand as 'green oxidation catalyst' that result in high aqueous stability in low pH. Further, the stability towards oxidative degradation and reactivity is controlled by modulating the σ-donor ability of the deprotonated amide nitrogen atoms in the six membered ring of transition metal complex of a biuret-amide based macrocyclic ligand. Moreover, in an attempt to make robust catalyst, the present inventor has observed that a modification at the aromatic ring by introducing electron withdrawing groups can tame down the oxidative degradation and provide enhanced stability at lower pH.

Accordingly, the present invention provides deprotonated Me-substituted biurets that can act as excellent ligands for designing of functional peroxidase mimics.

Present invention disclose biocompatible metal (III) complex of a biuret-amide based macrocyclic ligand of the Formula (X), as green catalysts that exhibit both excellent reactivity for the activation of $H_2O_2$ and high stability at low pH and high ionic strength, $$[M^{III}L1].P \qquad \text{Formula X}$$

wherein

'M' is selected from group of elements that exhibit +3 oxidation states such as transition elements selected from Cr, Mn, Fe, Cu, Ni, Co etc; group III elements, inner transition elements such as lanthanides;

L1 is a biuret-amide based macrocyclic ligand;

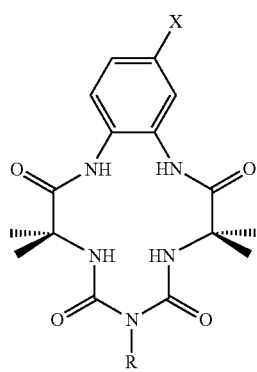

L1 wherein,
'X' represent hydrogen, electron withdrawing groups such as —$NO_2$, —COOH, —COOR, —COCl, —CN etc;
R represent C1-C3 alkyl or phenyl which may be optionally substituted;
P represent a cation selected from $Li^+$, $[Et4N]^+$ etc. The presence of cation $Li^+$ and $[Et4N]^+$ make the complex water soluble. The complex shows very good stability up to pH 2 in presence of $HClO_4$ and is stable up to 0.5M phosphate concentration.

In a preferred aspect, the present invention provides Fe (III) complex based on a macrocyclic biuret amide ligand of Formula (I) and its properties as a "green" oxidation catalyst.

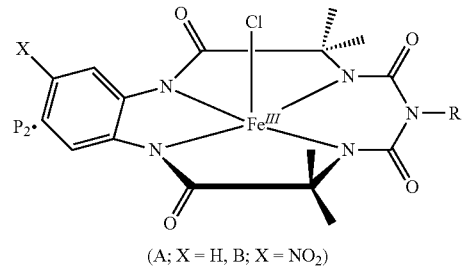

Formula I (A; X = H, B; X = $NO_2$)

wherein. 'X' represent hydrogen, electron withdrawing groups such as —$NO_2$, —COOH, —COOR, —COCl, —CN etc;
R represents C1-C3 alkyl or phenyl which may be optionally substituted;
P represent a cation selected from $Li^+$, $[Et_4N]^+$ etc.

In another aspect, the present invention discloses macrocyclic biuret amide based ligand L1 for designing functional peroxidase mimics;

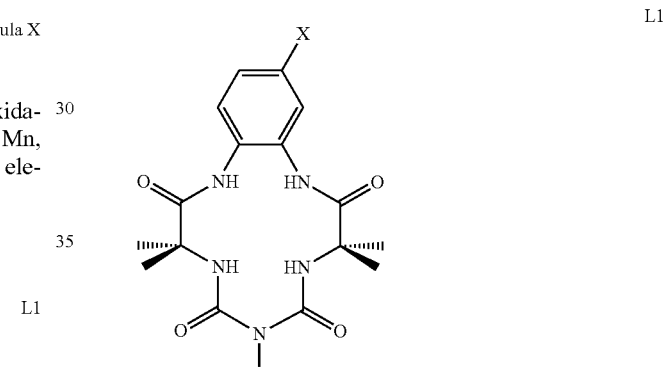

L1 wherein 'X' represent hydrogen, electron withdrawing groups such as —$NO_2$, COOH, COOR, —COCl, —CN etc;
R represents C1-C3 alkyl or phenyl which may be optionally substituted.

In an aspect, when X═H and R is methyl, the ligand L1 is represented by the Formula L1a;

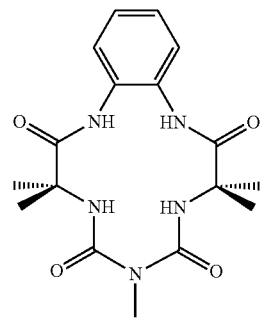

L1a

In yet another aspect, when X═$NO_2$ and R is methyl, the ligand L1 is represented by the formula L1b;

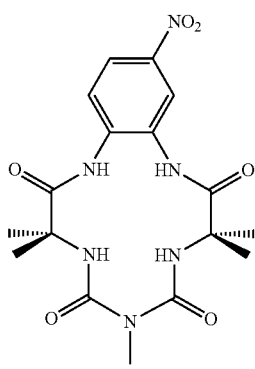

L1b

In another preferred aspect, the present invention provides a simple, high yielding synthesis of transition metal (III) complex based on macrocyclic biuret amide ligand.

The metal (III) complex based on a macrocyclic biuret amide ligand act as green catalysts for $H_2O_2$ oxidation of a wide spectrum of targets including but not limited to toxic polychlorophenols, thiophosphate pesticides and nitrophenols, azo dyes, dibenzothiophenes, an anthrax surrogate, and natural and synthetic estrogens, in effluent bleaching, in small molecule synthesis by oxidation (e.g. N-oxides, epoxides, aldehydes and the like may be synthesized from the oxidation of suitable precursor molecules). In the absence of other reducing agents the transition metal (III)-complex of present invention can catalytically convert $H_2O_2$ into dioxygen. The metal (III) complex activators of the invention are reactive, low molecular weight, functioning analogues of catalase-peroxidase enzymes.

The Fe(III)-complex based on a macrocyclic biuret amide ligand act as green catalysts for $H_2O_2$ oxidation of a wide spectrum of targets including but not limited to toxic polychlorophenols, thiophosphate pesticides and nitrophenols, azo dyes, dibenzothiophenes, an anthrax surrogate, and natural and synthetic estrogens, in effluent bleaching, in small molecule synthesis by oxidation (e.g. N-oxides, epoxides, aldehydes and the like may be synthesized from the oxidation of suitable precursor molecules). In the absence of other reducing agents the Fe(III)-complex of present invention can catalytically convert $H_2O_2$ into dioxygen. The Fe (III) complex activators of the invention are reactive, low molecular weight, functioning analogues of catalase-peroxidase enzymes.

In another preferred embodiment, the present invention relates to a simple high yielding synthesis of library of metal (III) complex based on a macrocyclic biuret amide ligand including the following steps:

1. cyclizing diamine (1) with N,N-dichloroformyl(aryl/alkyl)amine (2) dissolved in dry THF, base and chloroform at 0° C. under nitrogen, allowing to warm to room temperature (25 to 35° C.), stirring for about 12 hours to obtain macrocylic biuret-amide ligand of Formula L1; and
2. inserting metal (III) using metal precursor into the biuret-amide ligand L1 in presence of a base and non-polar solvent followed by addition of a cationic salt by a process known in the art.

According to the process, diamine (1) is added to a mixture of dry THF and dry base selected form diethylamine, triethylamine etc. and the resultant solution is added into an addition funnel. N,N-dichloroformyl(aryl/alkyl)amine (2) is diluted with dry THF and transferred into another addition funnel. Both the solutions are added drop wise over a period of 1 hour into three necked round bottom flask containing dry THF at 0° C. under $N_2$. After complete addition, the reaction mixture is allowed to warm to room temperature, stirred for an additional 12 hours till completion of the reaction. The reaction mixture is concentrated, purified by a flash column chromatography to obtain pure macrocylic ligand L1.

To the macrocyclic ligand L1 dissolved in dry THF is added n-BuLi at 0° C. under Argon (Ar) followed by addition of solid anhydrous metal precursor under positive argon flow. The reaction is allowed to proceed under Ar at room temperature for 12 hours after which it is opened to air to yield a dark orange-brown precipitate. The precipitate is filtered through a filter and dissolved in lower alcohol such as methanol to afford an orange solution. The solution containing the complex is loaded onto a cationic ion-exchange resin column that had been presaturated with [Et4N]$^+$. The orange band is eluted with methanol and the solvent is removed under reduced pressure to yield a red-orange solid. Further purification is achieved by column chromatography using basic alumina with CH2Cl2:MeOH:99:1 as the eluent. X-ray diffracting quality crystals are obtained by slow vapor diffusion of diethyl ether into the solution of the complex in acetonitrile.

The process is schematically given below:

Scheme1: Synthesis of macrocyclic biuret based ligand (L1) and its corresponding metal (III) complex (I)

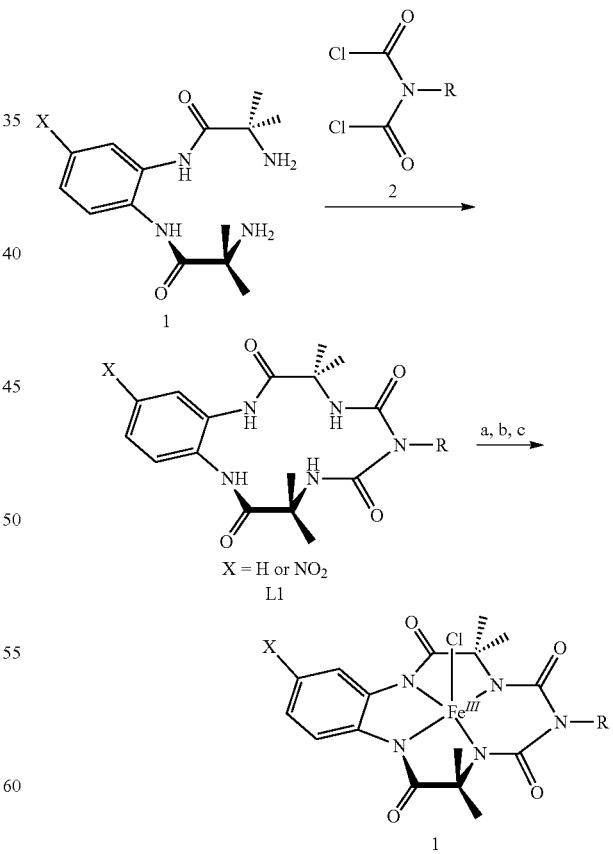

a. n-Butyl lithium
b. FeCl$_2$
c. O$_2$, Et$_4$NCl

In another embodiment, the present invention relate to synthesis of library of Fe (III) complex based on a macrocyclic biuret amide ligand;

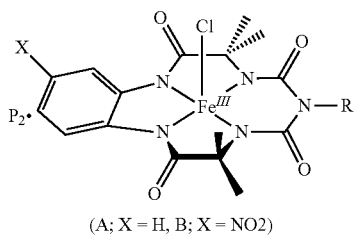

Formula 1

(A; X = H, B; X = NO2)

wherein, 'X' represent hydrogen, electron withdrawing groups such as —NO2, —COOH, —COOR, —COCl, —CN etc; R represents C1-C3 alkyl or phenyl which may be optionally substituted; P represent a cation selected from $Li^+$, $[Et_4N]^+$.
comprising;
  i. cyclizing diamine (1) with N,N-dichloroformyl(aryl/alkyl)amine (2) dissolved in dry THF, base and chloroform at 0° C. under nitrogen, allowing to warm to room temperature, stirring for about 12 hours to obtain macrocylic biuret-amide ligand of Formula L1; and
  ii. inserting Fe (III) into the biuret-amide ligand (L1) using $FeCl_2$ in presence of a base n-butyl lithium and non-polar solvent followed by addition of $Et_4N^+Cl^-$ by a process known in the art.

Figure 2:
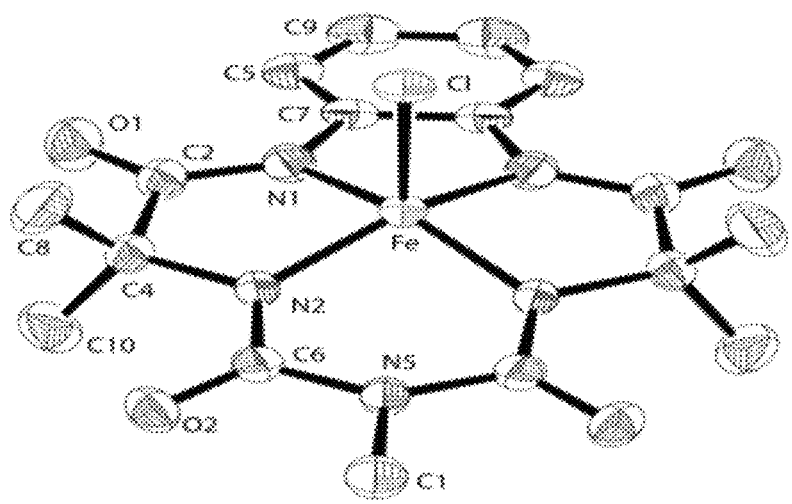
FIG. 2 depicts an ORTEP (Oak Ridge Thermal Ellipsoid Plot Program) diagram of the anionic part of (IA). H-atoms are not shown for clarity.

Fe (III) complex $(Et_4N)_2 \cdot [Fe^{III}(biuret\text{-}amide)]$ (IA) obtained by the process described above is characterized by Single crystal X-ray diffraction to observe the molecular packing in crystal lattice. The X-ray crystal structure of (IA) indicates a square pyramidal Fe(III) with an axial Cl atom that has been also observed for other Fe-TAML's (FIG. 2).

The Fe—N bond length is 1.88(2) Å and the Fe(III) lies 0.448 Å above the plane formed by the four donor nitrogen's (NA, NB, NC, ND). The N5 atom of the Me-biuret ring is 3.14(3) Å away from the Fe(III) indicating that this N-atom is not involved in bonding with the Fe(III) center. The Me-biuret ring is very planar and the torsion angle between the C1-N5 and C6-N2 planes is around −175.13°. Therefore the N5 atom in the 6-membered ring is strictly sp2 hybridized and the nitrogen lone pair, residing in the p orbital of N5 atom, is conjugated extensively to the carbonyl C-atom on both sides.

Figure 3:
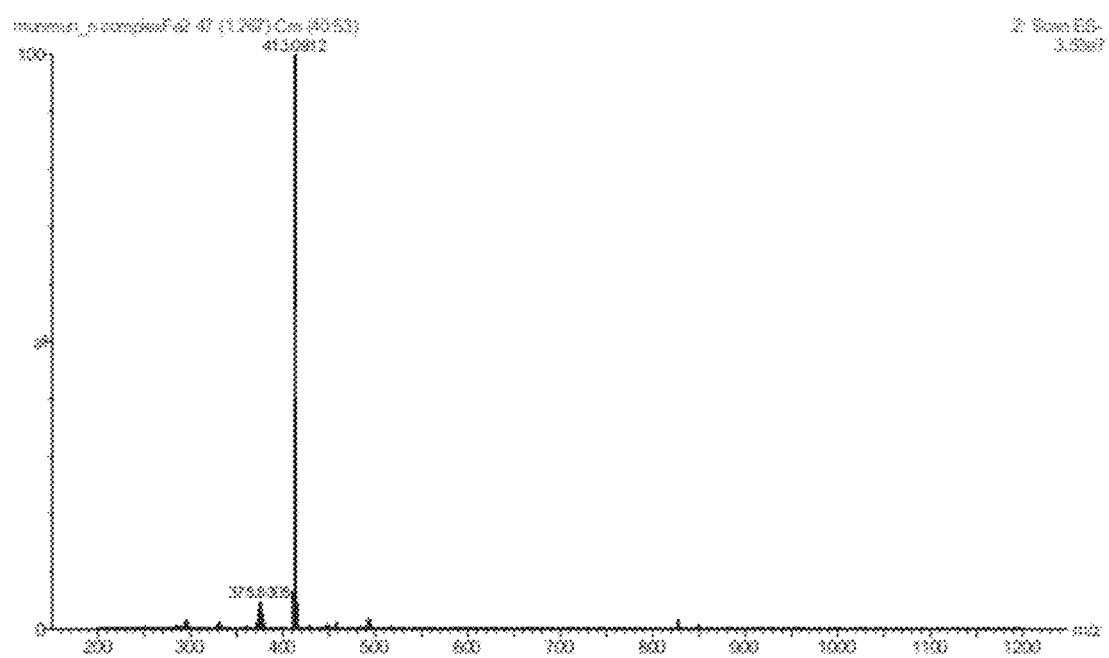
FIG. 3 depicts ESI-MS (electrospray ionization mass spectrometry) of a solution of complex 1A in methanol (m/z 413). The axial chloro ligand is not observed as this ligand is labile and gets dissociated under the conditions of the mass spectrometry experiment.
Figure 4:
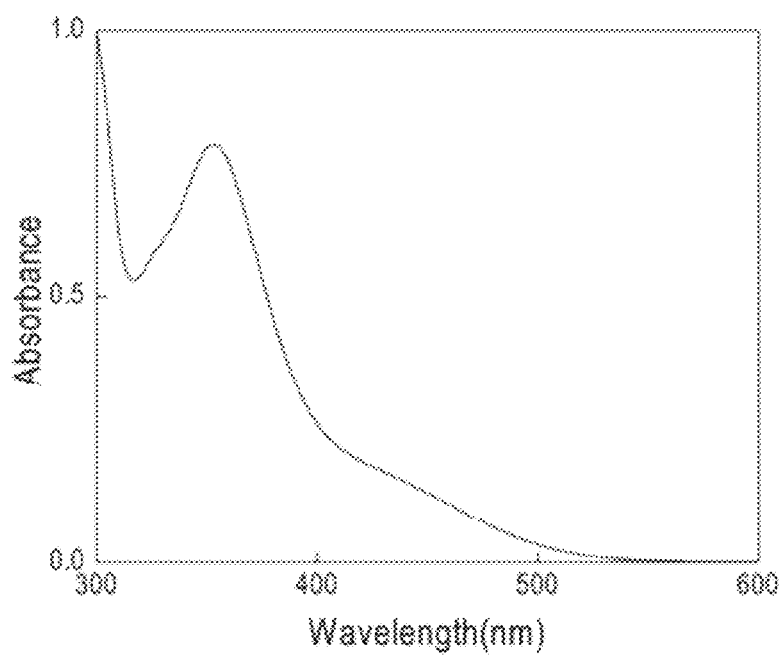
FIG. 4 depicts UV-Visible spectra of IA in water (0.138 mM).
Figure 5:
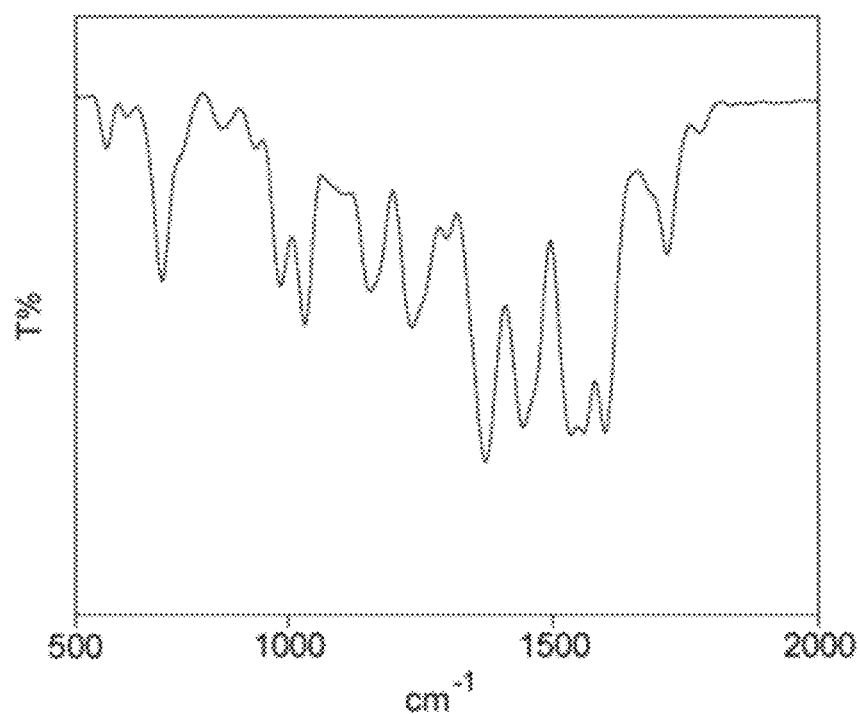
FIG. 5 depicts FT-IR Spectra of IA.

The complex is further characterized by ESI-MS (FIG. 3), UV-VIS (FIG. 4), FT-IR (FIG. 5) and elemental analysis.

Figure 6:
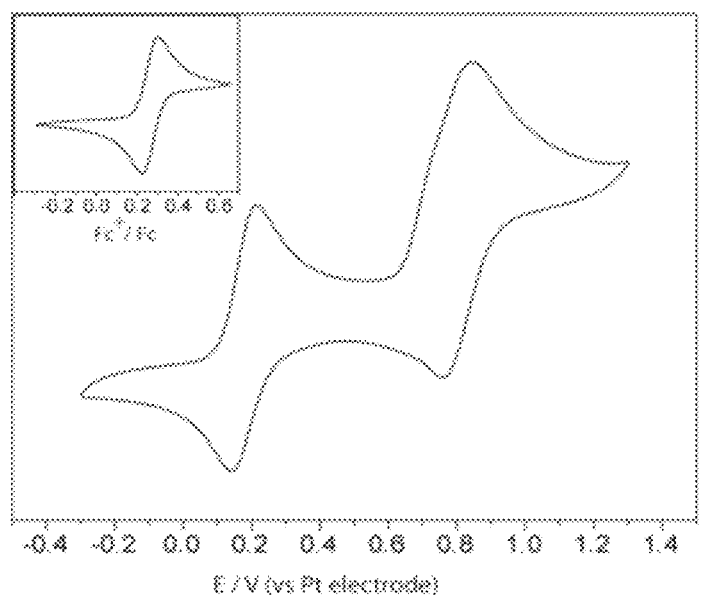
FIG. 6 depicts Cyclic voltammogram of 1A vs Pt wire in CH$_3$CN (0.1 M n-Bu$_4$NPF$_6$, sweep rate 100 mV/see). The Fc$^+$/Fc couple under the same experimental condition is shown in inset.

The σ-donor ability of $(Et_4N)_2.[Fe^{III}(biuret\text{-}amide)]$ is studied using cyclic voltammetry. The cyclic voltammetry of (IA) in acetonitrile containing 0.1 M [n-Bu4N]PF6 as the supporting electrolyte shows one reversible process with formal reduction potential E1/2 at −0.064 V (vs Fe+/Fe; ΔEp=70 mV) and another quasi-reversible process with E1/2 at −0.559 V (vs Fe+/Fc; ΔEp=85 mV). The peak observed for (IA) (E1/2 at −0.064 V) can most likely be assigned to a one electron oxidation for a Fe(III)/Fe(IV) couple while the other peak might be due to a ligand centered oxidation process (FIG. 6). On comparison with Fe-TAML complex (II) where a —CMe2 group is present instead of a —NMe group in the six membered ring of the complex, the Fe(III)/Fe(IV) couple for (IA) is found to be approximately 230 mV lower. This indicates that presence of the —NMe group increases the donor ability of the amide nitrogen in the six membered ring of the macrocyclic complex.

Figure 7:
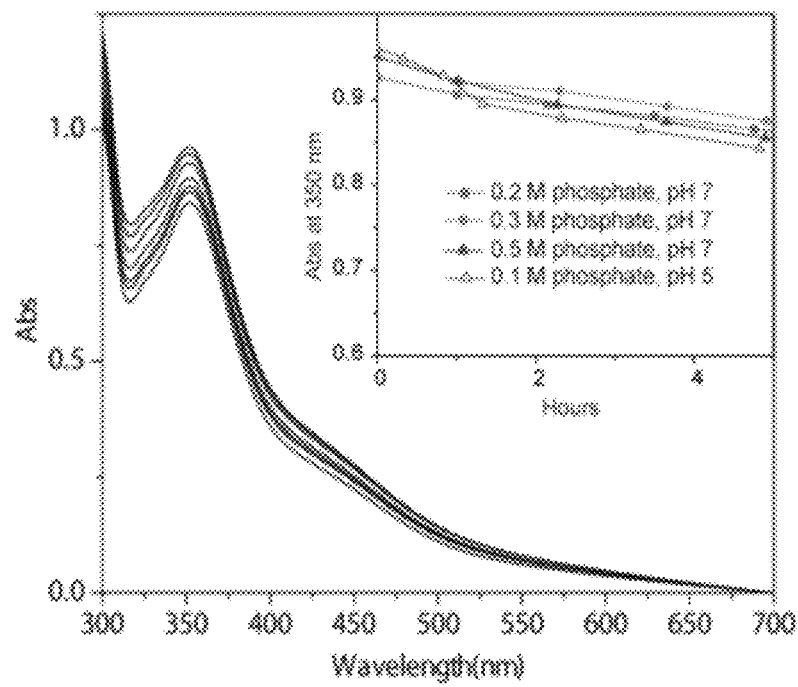
FIG. 7 depicts the Changes in UV-VIS spectra of (IA) (0.173 mM) in pH 5 phosphate buffer (0.1 M) over a period of 5 hrs at 25° C. (Inset) Kinetics of demetallation of IA in pH 7 phosphate buffer at various ionic strengths.

In yet another embodiment, the stability of (IA) towards demetallation at different pH and ionic strengths is tested to evaluate the operational stability of the complex of instant invention for possible catalytic reactions in water. The complex showed very good stability up to pH 2 in presence of $HClO_4$. Fe-TAML's are known to degrade in the presence of phosphate buffer and hence the stability of the complex (IA) is also tested under different ionic strengths and pH's. FIG. 7 shows the UV-VIS spectra of (IA) in the presence of pH 5 (0.1M phosphate buffer) over a time period of 5 hours at 25° C. It is found that only 10% of the complex degraded this time period. The $t_{1/2}$ was calculated to be approximately 18 hrs. The stability of this complex is also monitored at different ionic strengths at pH 7. The complex is found out to be remarkably stable up to 0.5 M phosphate concentrations (FIG. 7). The phosphate buffer induced demetallation for similar Fe-TAML's have been studied in details. The proposed mechanism for phosphate buffer induced demetallation involves first the co-ordination of the O—$PO(OH)_2$ into the Fe(III) center followed by the intramolecular attack of the H+ onto the amide N-donors. Complex (IA) has an extra —NMe group which is not bonded to the Fe(III) center. The lone pair on this N-atom resides predominantly in the p-orbital and can possibly be the first site for attack of the intramolecular H+ ion, thereby shielding complex (IA) from phosphate induced demetallation.

Figure 8:
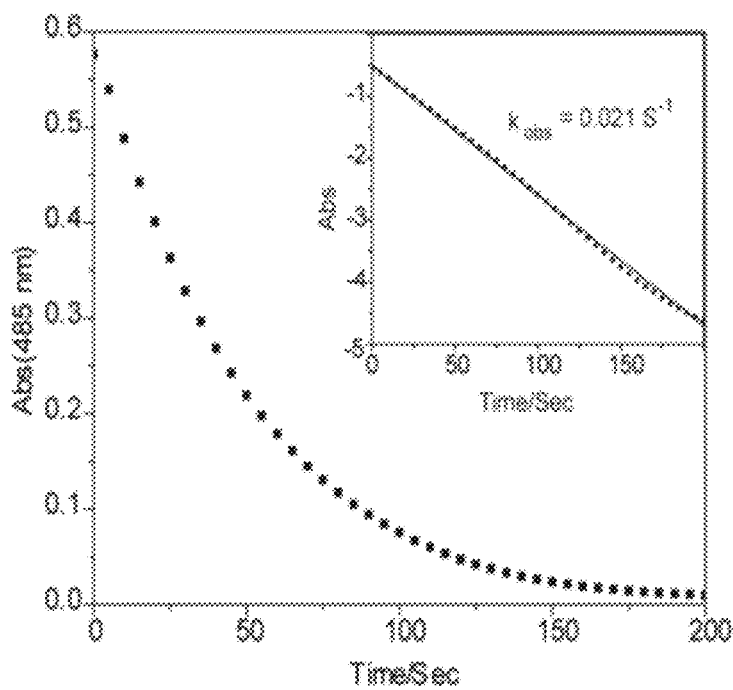
FIG. 8 depicts Bleaching of Orange II by (IA) at pH 11. (Inset) The kinetics of bleaching follows exponential kinetics.
Figure 9:
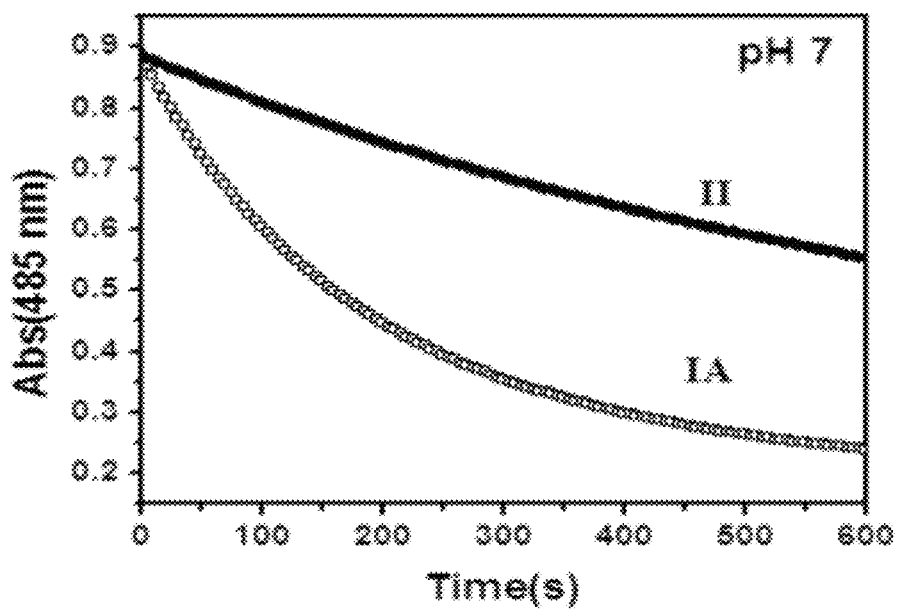
FIG. 9 depicts Comparative Orange II bleaching by H$_2$O$_2$ at pH 7 for (IA) and (II). [Catalyst]=2×10$^{-7}$ M, [H$_2$O$_2$]= 0.0015 M, [Orange II]=5×10$^{-5}$ M; 0.01 M phosphate buffer, 25° C.
Figure 10:
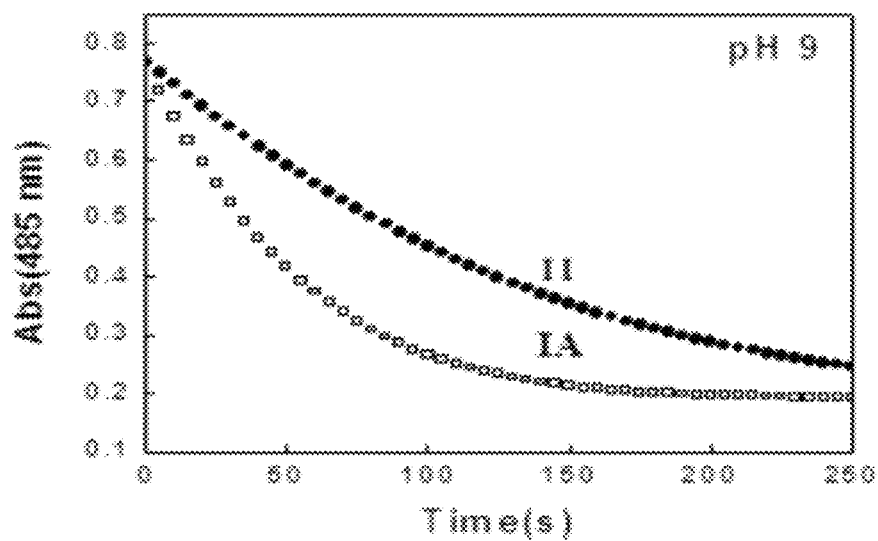
FIG. 10 depicts Comparative Orange II bleaching by H$_2$O$_2$ at pH 9 for (IA) and (II). [Catalyst]=2×10$^{-7}$ M, [H$_2$O$_2$]= 0.0015 M, [Orange II]=4×10$^{-5}$ M; 0.01 M phosphate buffer, 25° C.

In another embodiment, to study the efficacy of complex (IA) as $H_2O_2$ activating catalyst, its activity towards bleaching of the dye Orange II ([4-[(2-hydroxynaphthyl)azo]-benzene sulphonic acid], Na+ salt) is studied. At pH 11, the complex of the present invention, (IA) is found to be very efficient in activation of $H_2O_2$ for complete bleaching of the dye Orange II. The exponential kinetic curve, that holds for at least 6 half-lives (FIG. 8), indicates the fact that (IA) is oxidatively robust. Therefore, little or no degradation of the catalysts takes places during the course of the oxidation. This is because C—H bond of the —NMe group is situated very far away from the proposed Fe-oxo intermediate, thereby reducing the chances of ligand degradation by intramolecular C—H abstraction as has been proposed before for other Fe-TAML, complexes. The pseudo first order rate constant $k_{obs}$, calculated to be 0.021±0.001 s$^{-1}$, shows that catalytic rates to be comparable to the most efficient Fe-TAML catalysts. Comparison of the catalytic activity of the complex (IA) and Fe-TAML for the bleaching of Orange II at pH 7 and 9 shows that (IA) is much faster in oxidizing Orange II (FIGS. 9 and 10). Hence the substitution of the —CMe2 group in the malonyl fragment of Fe-TAML, with the —NMe group yields a catalysts which is a very good peroxidase mimic having very high reaction rates.

In yet another embodiment, the present invention provides $(Et_4N)$. robust Fe(III) complex of nitro ligated biuret amide macrocyclic ligand as given below.

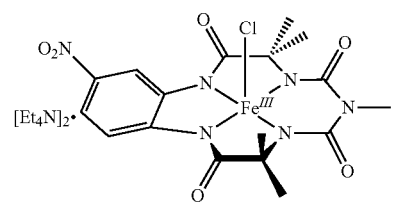

IB

Figure 11:
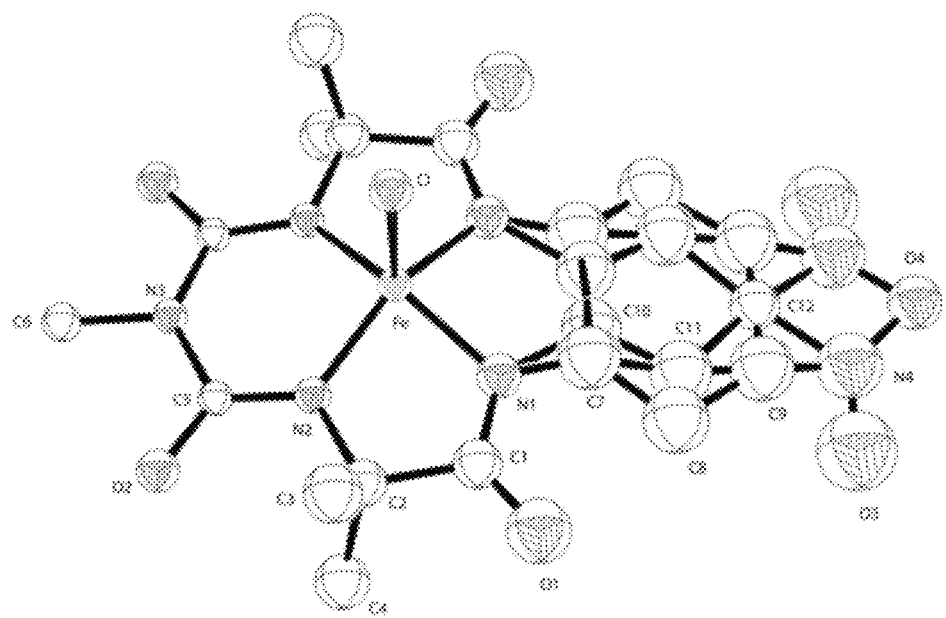
FIG. 11 depicts an ORTEP diagram of IB. H-atoms are not shown for clarity.

The preparation, reactivity and kinetics of robust Fe(III) complex of nitro ligated biuret amide macrocyclic ligand (IB)

towards orange II dye is given in the experiments below. The crystal structure and CV of Fe(III) complex of nitro ligated biuret amide macrocyclic ligand (IB) is given in FIG. 11 and FIG. 6 respectively.

In yet another embodiment, the present invention relate to the comparative study of compound of Formula IB and IA (wherein, X=H) w.r.t kinetics of acid induced demetalation, catalyzed bleaching of orange II dye, catalyzed bleaching of safranine O by $H_2O_2$ compound B*[Fe(III) complex of TAML]. The details are given below in the experiments.

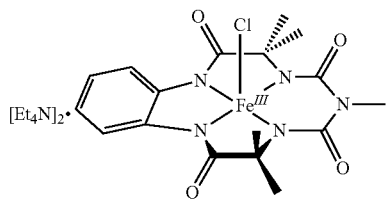

IA

The major catalytic steps, acid induced demetalation steps and mica or intermolecular oxidative degradation process is shown below in Scheme 2:

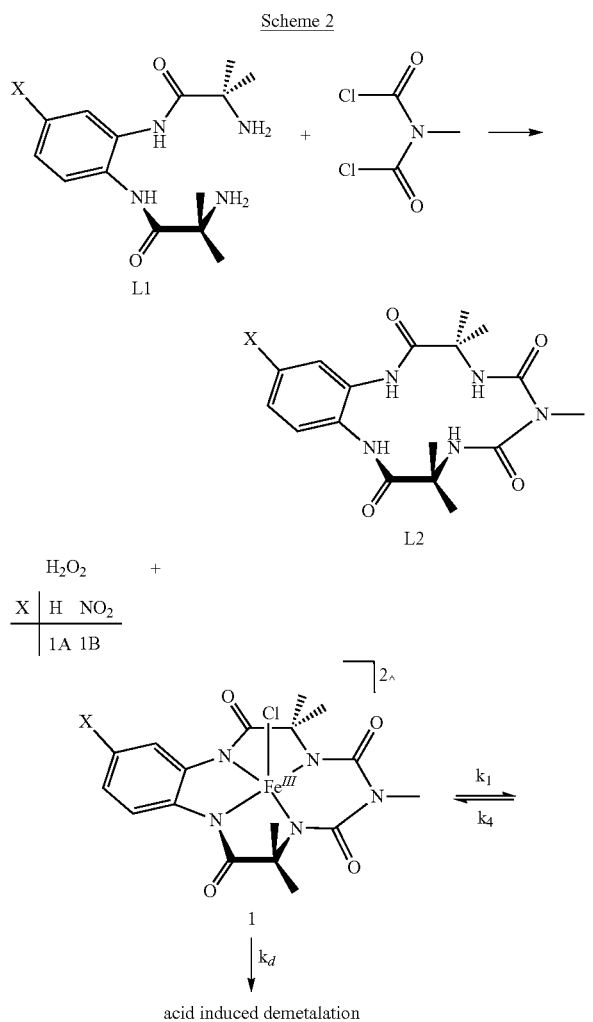

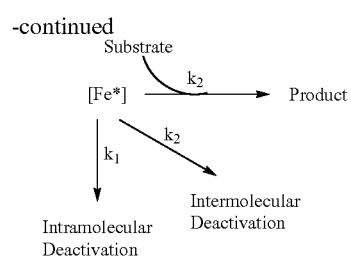

In another preferred embodiment, the present invention discloses the formation of a more stable $Fe^V$-oxo species that is generated by reaction of mCPBA and [FeIII(biuret-amide)] which is more oxidizing than $Fe^{IV}$-oxo and its use for oxidation of an unactivated C—H bonds (Scheme 3).

Scheme 3: Generation of $Fe^V$-oxo species and C—H bond oxidations

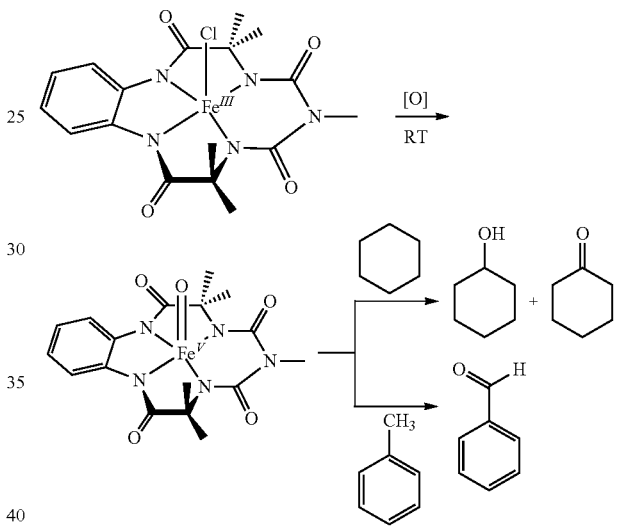

EXAMPLES

The following examples are given by way of illustration, therefore should not be construed to limit the scope of the invention.

Example 1

Step 1: Synthesis of (L1a)

3,3,6,9,9-pentamethyl-1,4,8,11-tetrahydro-1H-benzo[i][1,4,6,8,11]pentaazacyclotridecine-2,5,7,10(6H,11H)-tetraone Compound 1 (diamine, X=H) (44.83 mg, 287.41 μmol) was added to 20 mL dry THF with dry Et3N (100.15 mL, 718.52 μmol, 2 eq) and the resultant solution was transferred into an addition funnel. N,N-dichloroformylmethylamine (0.031 mL, 287.41 μmol, 0.8 eq) was diluted with 20 mL dry THF and was transferred into another addition funnel. Both these solutions were added drop wise over a period of 1 hr into a 100 mL 3-necked round bottom flask containing 20 mL of dry THF at 0° C. under N2. After the addition was complete, the reaction mixture was allowed to warm to room temperature (27° C.) and then stirred for an additional 12 hr. After completion of the reaction, the reaction mixture was concentrated and then purified by a flash column chromatography to obtain the macrocylcic ligand L1a. Yield: 39%.

Elemental analysis. Found: C, 56.44; H, 6.31; N, 19.140%. Calc. for $C_{17}H_{23}N_5O_4$: C, 56.50; H, 6.41; N, 19.38%. IR (KBr, vmax/cm-1): 3348 (s, NH), 3245 (s, NH), 1711 (s, CO), 1652 (s, CO), 1H NMR δH (200 MHz; CD3OD): 9.11 (s, 2H, NH), 7.99 (s, 2H, NH), 7.62 (dd, 2H, J1=3.5 Hz, J2=6.1 Hz, Ph), 7.21 (dd, 2H, J1=3.6 Hz, J2=6.0 Hz, Ph), 3.00 (s, 3H, CH3), 1.54 (s, 12H, CH3), 13C NMR; δC (d6 DMSO 200 MHz): 173.6, 156.6, 130.86, 125.6, 59.0, 31.8, 25.5. ESI-MS: m/z 360.3 (M-H+, 100%).

Example 1

Step 2: Synthesis of $(Et_4N).[Fe^{III} \text{ biuret-amide}]$ (1A)

Tetraethyl ammonium 3,3,6,9,9-pentamethyl-1,4,8,11-tetrahydro-1H-benzo[i][1,4,6,8,11]pentaazacyclotridecine-2,5,7,10(6H,11H)-tetraone ferrate To a solution of compound L1a (50 mg, 0.138 mmol) in 10 ml of dry THF was added n-BuLi (0.4 ml of 1.4 M solution in hexane, 0.567 mmoles, 4.4 eq) at 0° C. under Ar. Solid anhydrous $FeCl_2$ (21.1 mg, 0.166 mmoles, 1.2 eq) was then added as a solid into this solution under positive argon flow. The reaction was allowed to proceed under Ar at room temperature (30° C.) for 12 hours after which it was opened to air to yield a dark orange-brown precipitate. The precipitate was filtered through a fit and was dissolved in methanol to afford an orange solution. The solution (5 ml) containing the complex was loaded onto a cationic ion-exchange resin (Amberlite-120) column that had been presaturated with $[Et_4N]^+$. The orange band was eluted with methanol and the solvent was removed under reduced pressure to yield a red-orange solid. Further purification was achieved by column chromatography using basic alumina with $CH_2Cl_2$:MeOH:99:1 as the eluent. X-ray diffracting quality crystals were obtained by slow vapor diffusion of diethyl ether into the solution of the complex in acetonitrile. Yield: 60 mg (79%).

Elemental analysis. Found: C, 55.71; H, 8.14; N, 13.688%. Calc. for $C_{33}H_{59}N_7ClFeO_4$: C, 55.85; H, 8.32; N, 13.820; Fe, 8.03%. UV-VIS: $\lambda_{max}$(MeOH)/nm; 360 ($\epsilon$/dm$^3$ mol$^{-1}$ cm$^{-1}$, 3990), IR (KBr, $v_{max}$/cm$^{-1}$): 1601 (s, CO), 1556 (s, CO), 1531 (s, CO). ESI-MS (negative ion mode): m/z 413.1 (M-H$^+$, 100%).

Example 2

Step 1: Synthesis of (L1b)

3,3,6,9,9-pentamethyl-13-nitro-1,4,8,11-tetrahydro-1H benzo[i][1,4,6,8,11]pentaazacylotridecine-2,5,7,10(6H,11H)-tetraone 100 mg of compound 1 (X=$NO_2$, 0.309 mmol) was added to 20 mL dry THF with dry Et3N (0.086 ml, 0.619 mmol, 2 eq) and the resultant solution was transferred into an addition funnel N,N-dichloroformylmethylamine (0.027 ml, 0,247 mmoles, 0.8 eq) was diluted with 20 mL dry THF and was transferred into another addition funnel. Both these solutions were added drop wise over a period of 1 hr into a 100 mL 3-necked round bottom flask containing 20 mL of dry THF at 0° C. under N2. After the addition was complete, the reaction mixture was allowed to warm to room temperature (25° C.) and then stirred for an additional 12 hr. After completion of the reaction, the reaction mixture was concentrated and then purified by a flash column chromatography (100% EtOAc) to yield macrocyclic biuret based ligand (L1b). Yield: 55 mg (44%).

Elemental analysis. Found: C, 56.44; H, 6.31; N, 19.140%. Calc. for C17H22N6O6: C, 50.24; H, 5.46; N, 20.68%. IR (KBr, vmax/cm-1): 3348 (s, NH), 3245 (s, NH), 1711 (s, CO), 1652 (s, CO). 1H NMR δH (200 MHz; DMSO-d6): 9.53 (s, 1H, NH), 9.38 (s, 1H, NH), 8.36 (d, 1H, J=2.73 Hz, Ph), 8.19 (m, 2H. NH & Ph), 8.08 (d, 1H, J=8.96, Ph), 7.97 (s, 1H, NH), 3.01 (s, 3H, CH3), 1.56 (d, 12H, J=2.31 Hz CH3). 13C NMR; δC (d6 DMSO 200 MHz): 173.6, 156.6, 130.86, 125.6, 59.0, 31.8, 25.5. ESI-MS: m/z 407.18 (M-H+, 100%), Example 2

Step 2: Synthesis of $(Et_4N)_2[Fe^{III}(\text{nitro ligated biuret-amide})]$(1B)

Tetraethyl ammonium 3,3,6,9,9-pentamethyl-13-nitro-1,4,8,11-tetrahydro-1H benzo[i][1,4,6,8,11]pentaazacyclotridecine-2,5,7,10(6H,11H)-tetraone ferrate To a solution of compound L1b (25 mg, 0.061 mmol) in 10 ml of dry THF was added n-BuLi (0.193 ml of 1.4 M solution in hexanes, 0.270 mmoles, 4.4 eq) at 0° C. under Ar. Solid anhydrous $FeCl_2$ (9.36 mg, 0.073 mmoles, 1.2 eq) was then added as a solid into this solution under positive argon flow. The reaction was allowed to proceed under Ar at room temperature (35° C.) for 12 hours after which it was opened to air to yield a dark orange-brown precipitate. The precipitate was filtered through a frit and was dissolved in methanol to afford an orange solution. The solution (5 ml) containing the complex was loaded onto a cationic ion-exchange resin (Amberlite-120) column that had been presaturated with $[Et_4N]^+$. The orange band was eluted with methanol and the solvent was removed under reduced pressure to yield a red-orange solid. Further purification was achieved by column chromatography using basic alumina with $CH_2Cl_2$:MeOH:99:1 as the eluent. X-ray diffracting quality crystals were obtained by slow vapor diffusion of diethyl ether into the solution of the complex in acetonitrile. Yield: 60 mg (79%). Single crystals were obtained by layering hexane over acetone dissolved complex.

Elemental analysis. Found: C, 52.51; H, 7.66; N, 12.78%. Calc. For $C_{33}H_{58}N_8ClFeO_6$: C, 52.55; H, 7.69; N, 12.74. UV-Vis: λmax(H2O)/nm; 351 (ϵ/dm3 mol-1 cm-1, 5164), IR (KBr, vmax/cm-1): 1601 (s, CO), 1556 (s, CO), 1.531 (s, CO). ESI-MS (negative ion mode): m/z 458.1 (Negative ion mode, 100%).

Experimental

Materials

Hydrogen peroxide (30% w/w) was purchased from Merk, India while Orange II dye and Safranine O were bought from Aldrich. Orange II was used without further purification whereas Safranine O was recrystallized from ethanol and used in the kinetics. Other reagents used in experiments were also supplied by Aldrich. Deionized water was used to make all the stock solutions for the kinetic and spectrophotometric runs.

[I]. Physical Measurements.

All the synthetic organic products were characterized by $^1H$ and $^{13}C$ NMR spectra measured on a Bruker (200 MHz) spectrometer & these data are reported in δ(ppm) vs (CH3)4Si with the deuterated solvent proton residuals as internal standards. Infrared spectra were obtained on a Perkin-Elmer FT-IR spectrum GX instrument. LC-MS from Acquity Waters was used for ESI-MS analysis. EPR spectrum was recorded on a Bruker EMX X-band spectrometer operating at a field modulation of 100 kHz, modulation amplitude of 2. G and microwave radiation power of 2 mW. The solid Fe(III) complex was taken in a quartz tube and the spectrum was recorded at 298K. Cyclic voltammetry (CV) was done on an Autolab PGSTAT30 (Eco-Chemie) instrument in a conventional three-electrode test cell with platinum as the working electrode (WE), platinum wire as quasi reference electrode (RE) and a platinum foil as a counter electrode (CE). The measurements were carried out using a solution of 1 mM of (I) in dry acetonitrile with 0.1 M [n-Bu4N]PF6 as the supporting electrolyte. All reversible couples were confirmed by a linear dependence of peak current vs. the square root of the scan rate over the range of 20-200 mVs$^{-1}$.

Figure 18:
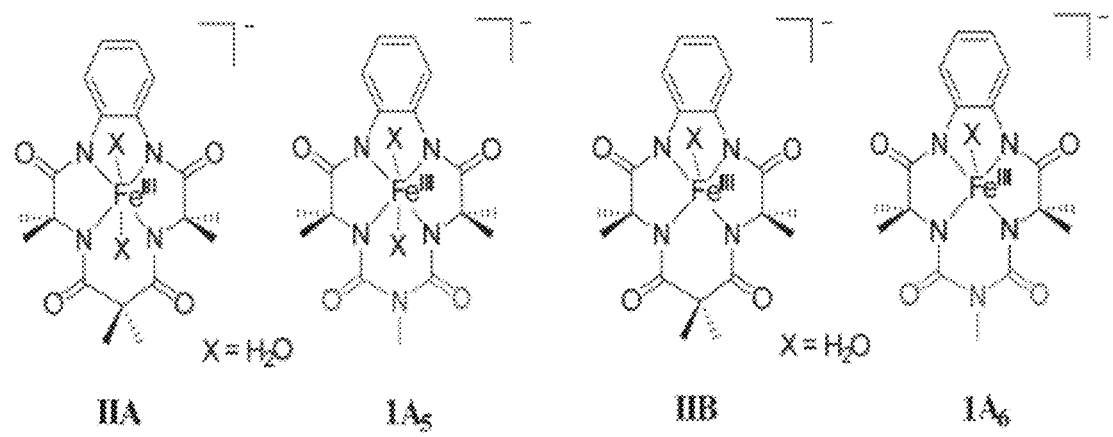
FIG. 18 depicts Six coordinated and five coordinated complexes of II and IA.

[II] Computational Details:

The six coordinated complexes IIA and $1A_6$, as well as their five coordinated analogues, IIB and $1A_5$, (FIG. 18) were optimized with density functional theory (DFT); using the Gaussian 09 suite of programs (M. J. Frisch, G. W. Trucks; H. B. Schlegel, G. E. Scuseria, M. A. Robb, J. R. Cheeseman, G. Scalmani, V. Barone, B. Mennucci, G. A. Petersson, Nakatsuji, M. Caricato, X. Li, H. P. Hratchian A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T, Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M, Cossi, N. Rega, J. M. Millam, K. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, and D. J. Fox, Gaussian 09, Revision B.01; Gaussian, Inc., Wallingford Conn., 2009.) The 6-31 g* basis set (Hariharan, P. C.; Pople, J. A. Chem. Phys. Lett. 1972, 16, 217) and b31yp functional ((a) Becke, A. D. J. Chem. Phys. 1993, 98, 5648. (b) Stevens, P. J.; Devlin, F. J.; Chablowski, C. F.; Frisch, M. J. J. Phys. Chem. 1994, 80, 11623.) were employed. The charges on the atoms were calculated by the Mulliken Population analysis. Unrestricted calculations were done for all the complexes and the spin contamination was found to be negligible.

In order to do a comparison of the possible protonated conformers for the five coordinated complexes IIB and $1A_5$, further DFT calculations were done with the Turbomole suite of programs, using Turbomole Version 6.0. (R, Ahlrichs, M, Baer, M. Haeser, H. Horn, C. Koelmel, Chem. Phys. Lett. 1989, 162, 165-169). The geometry optimizations were performed using the Perdew, Burke, and Erzenhof density functional (PBE) (J. P. Perdew, K. Burke, M. Emzerhof, Phys. Rev. Lett. 1996, 77, 3865). The electronic configuration for all the atoms was described by a triple-zeta basis set augmented by a polarization function (TURBOMOLE basis set TZVP). (a F. Weigend, Physical Chemistry Chemical Physics 2002, 4, 4285-4291; b F. Weigend, R. Ahlrichs, Physical Chemistry Chemical Physics 2005, 7, 3297-3305; c A. Schaefer, H. Horn, R. Ahlrichs, Journal of Chemical Physics 1992, 97, 2571-2577; d A. Schaefer, C. Huber, R. Ahlrichs, Journal of Chemical Physics 1994, 100, 5829-5835) The resolution of identity (RI), (K. Eichkorn, O. Treutler, H. Oehm, M. Haeser, R. Ahlrichs, Chem. Phys. Lett. 1995, 240, 283-290.) along with the multipole accelerated resolution of identity (marij) (M. Sierka, A. Hogekamp, R. Ahirichs, J, Chem. Phys. 2003, 118, 9136-9148) approximations were employed for an accurate and efficient treatment of the electronic Coulomb term.

[III]. Kinetic Studies:

Acid induced demetalation kinetics was monitored in kinetic mode of the spectrophotometer (Perkin-Elmer—λ35) using 1.00 cm quartz cell in thermostatted cell housing. In the all kinetic runs IB was kept constant at 0.173 mM while acid concentration was varied from 0.04 to 3.0 M using $HClO_4$. The pseudo first order rate constants ($k_d$) were calculated from the initial rates at 350 nm (one of the absorption peaks of complex IB) and temperature was kept constant at 25.0±0.5° C. For each set, solution pH was measured with a pH meter (LABINDIA, PICO$^+$) with calibrated electrode.

Using same Perkin-Elmer spectrophotometer Orange II bleaching kinetics were carried out in 0.01 M phosphate buffer at 485 nm, one of the absorption peaks of Orange II. pH was varied from 7 to 11. Strength of stock solutions of IB and Orange II were ($2\times10^{-5}$ M) and ($2-20\times10^{-4}$ M) respectively. Stock solution of hydrogen peroxide of $2\times10^{-2}$ M was made by measuring the optical density at 230 nm ($\epsilon$=72.8 $M^{-1}$ $cm^{-1}$). Appropriate amount of stock solutions of Orange II, $Fe^{III}$-catalyst (IB) and $H_2O_2$ were added consecutively in the 1.00 cm quartz cell during experiments. Extinction coefficients for Orange II of 17,800, 23,000 and 19,400 $M^{-1}$ $cm^{-1}$ at pH 7, 9 and 11 respectively was used to calculate the initial rates of Orange II oxidation, Plot of concentration versus time was taken up to 10-20% of conversion of the dye compared to the total reaction.

Safranine O oxidation kinetics was monitored at 525 nm and pH 11 in 0.01 M Phosphate Buffer. The strengths of stock solutions of Safranine O, [Fe$^{III}$(biuret-amide)](X=H, $NO_2$) IA, IB complexes and hydrogen peroxide were respectively $2\times10^{-3}$ M, $5\times10^{-5}$ M and 0.2 M respectively. The extinction coefficient of $3.3\times10^4$ $M^{-1}$ cm at 525 nm was used to get initial rate in terms of concentration unit ($Ms^{-1}$). To get the intramolecular inactivation rate ($k_i$) absorbance change with time was monitored up to complete inactivation of the catalyst. Calculations of rate constants were performed by using Equation (4) and (5).

a. Kinetic Studies of Add Catalyzed Demetalation.

Figure 12:
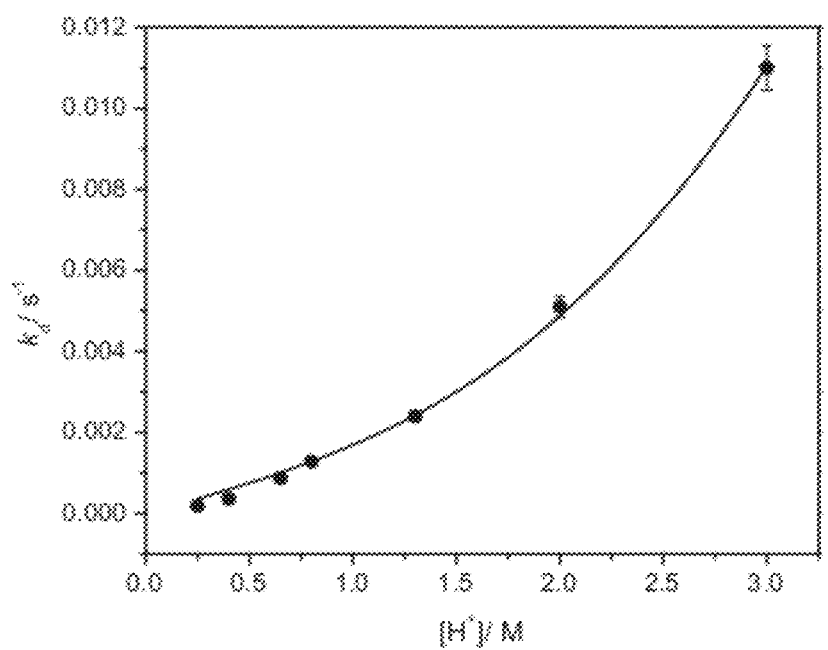
FIG. 12 depicts acid catalyzed demetalation of Fe(III) complex of nitro ligated biuret amide macrocyclic ligand (IB).

[Fe$^{III}$(biuret-amide)] catalyst are subject to H$^+$ catalyzed demetalation, following the Equation 1 according to Scheme 2 described above, $k_d=k_1*[H^+]+k_2*[H^+]^2+k_3*[H^+]^3$ where $k_d$ is the first order rate constant. Comparing the kinetic parameter it was found acid induced demetalation of IA and IB was significantly less compared to (compound II) complex i.e Fe (III) complex of TAML (tetraamido macrocyclic ligand) (Table 2). Kinetic fitting of Equation 1 for catalyst IB is given in FIG. 12. Demetalation in high concentration phosphate buffer was totally unimportant because in twenty four hour time scale insignificant absorption change was observed at 350 nm for both IA and IB.

$$k_d = \frac{k_1 K_{a1} K_{a2}[H^+] + k_2 K_{a2}[H^+]^2 + k_3[H^+]^3}{K_{a1}K_{a2} + K_{a2}[H^+] + [H^+]^2 - } \quad (1)$$
$$k_1^*[H^+] + k_2^*[H^+]^2 + k_3^*[H^+]^3$$

TABLE 2

Kinetic parameters of acid catalyzed demetalation of [Fe$^{III}$(L2X)](X = H, NO$_2$) IA, IB in comparison to compound II and compound II (with CF$_2$).

| Catalyst | $k_1^*$ [M$^{-1}$s$^{-1}$] | $k_3^*$ [M$^{-3}$s$^{-1}$] | $t_{1/2}$ [pH 1] |
|---|---|---|---|
| 1A | (3.7 ± 0.5) × 10$^{-3}$ | (1.04 ± 0.04) × 10$^{-1}$ | 144 Sec |
| 1B | (1.41 ± 0.09) × 10$^{-3}$ | (2.5 ± 0.1) × 10$^{-4}$ | 4788 Sec |
| II | 2.2 ± 0.7 | (6.7 ± 0.2) × 10$^5$ | 1.0 × 10$^{-3}$ Sec |
| II (CF$_2$) | (2.56 ± 0.03) × 10$^{-4}$ | (10.6 ± 0.5) × 10$^{-4}$ | | b. Kinetics of IA and IB Catalyzed Bleaching of Orange II by H$_2$O$_2$

Figure 19:
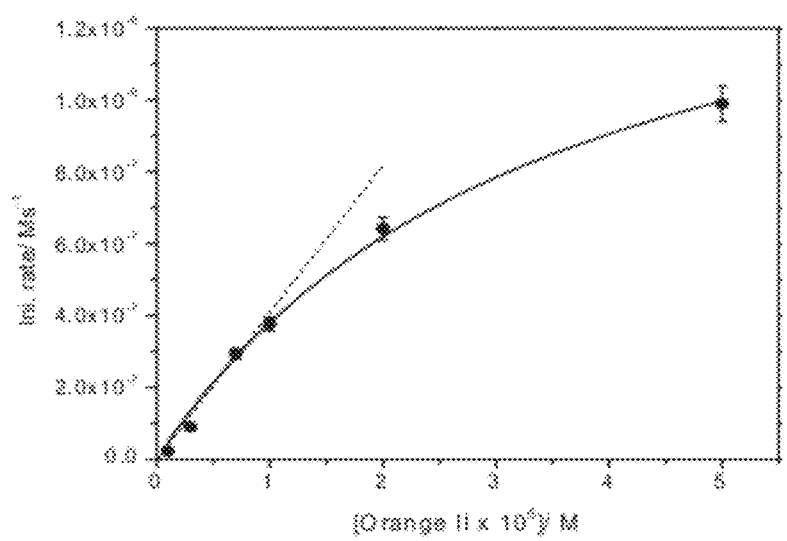
FIG. 19 depicts Initial rate/Ms$^{-1}$ was plotted as a function of [Orange II] at pH 11 in 0.01 M Phosphate Buffer, T=25° C. H$_2$O$_2$ and FeIII-catalyst concentration were kept constant at 7×10$^{-4}$ M and 01×10$^{-7}$ M respectively, Solid line was data fitted according to the Equation 2. Fitting results k$_1$= (2.4±0.2)×10$^4$ M$^{-1}$ s$^{-1}$, k$_{-1}$~0 and k$_2$=(4.9±0.5)×10$^5$ M$^{-1}$ s$^{-1}$. The dashed line passing through origin shows up to 1×10$^{-5}$ M of Orange II initial rate increases linearly holding the condition k$_1$[H$_2$O$_2$]>k$_2$[Orange II] as well as k$_1$[H$_2$O$_2$]>k$_{-1}$ which gives k$_2$=4.5×105 M$^{-1}$ s$^{-1}$.
Figure 20:
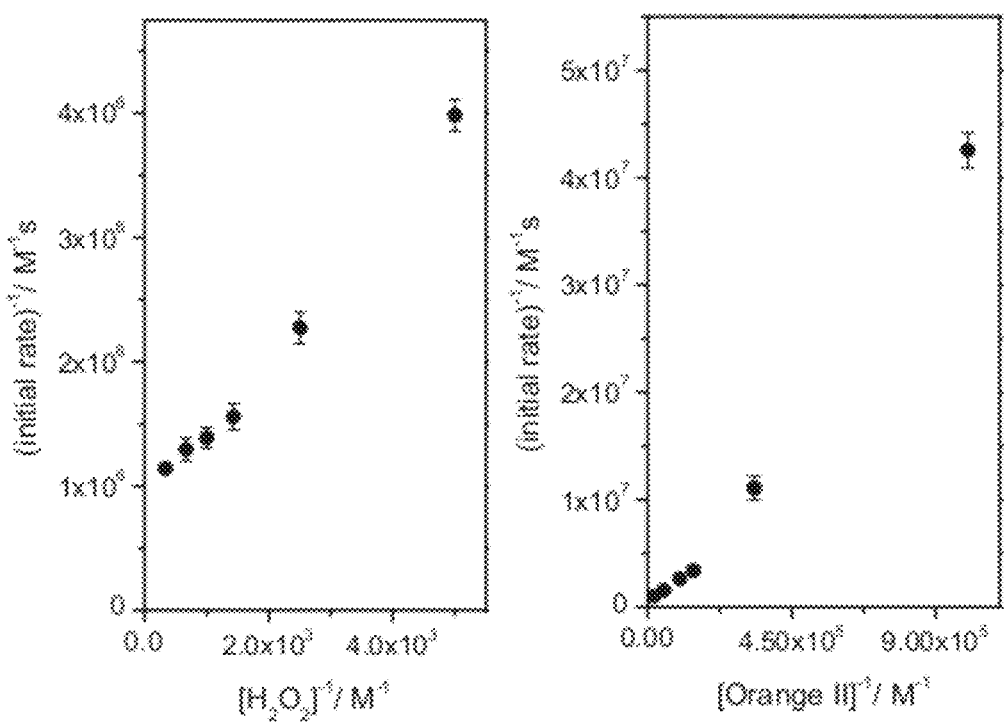
FIG. 20 depicts at pH 11, T=25° C. in 0.01 M Phosphate Buffer the inverse initial rate has linear dependence on inverse concentrations of Orange II and H$_2$O$_2$ up to 2×10$^{-5}$ M and 1×10$^{-3}$ M respectively, [IB]=1×10$^{-7}$ M during the reaction.
Figure 21:
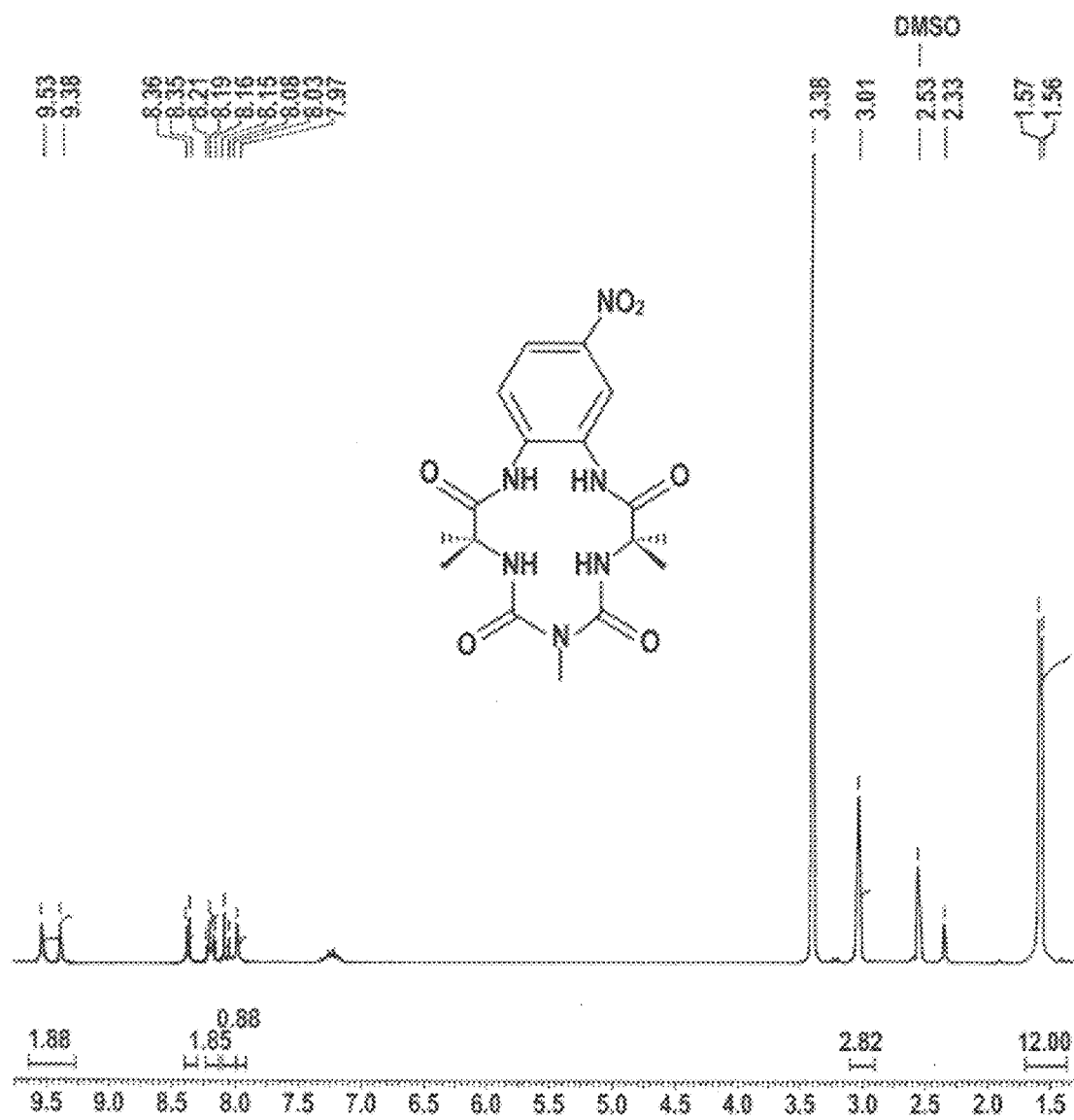
FIG. 21 depicts $^1$H NMR of L1b.

Orange II dye has absorption maxima at 485 nm. Natural oxidant H$_2$O$_2$ slowly oxidizes Orange II but in presence of IA and IB huge catalysis was observed. The kinetic data followed the mechanism shown in Scheme 2. The initial rate of the dye bleaching reaction obeyed Michaelis-Menten type Equation (2) which was derived considering the steady state of oxidized [Fe$^{III}$(L2X)] species using mass balance equation [Fe$^{III}$]T=[Fe$^{III}$(L2X)]]+ [Oxidized-Fe$^{III}$ L2X)]]. From kinetic fitting it was observed k$_{-1}$~0 for both IA and IB. At pH 11 the inverse initial rate has linear dependence on inverse concentrations of both the reagents which suggests, k$_{-1}$ is negligible (FIG. 19: up to 2×10$^5$ M for Orange II and 1×10$^{-3}$ M for H$_2$O$_2$ at [IB]=1×10$^7$ M). In Table 3 all the kinetic parameters related to Orange II bleaching are given in details at 25° C. in 0.01 M Phosphate Buffer.

$$\frac{d[Sub]}{dt} = \frac{k_1 k_2 [Fe^{III}]_{total}[H_2O_2][Sub]}{k_{-1} + k_1[H_2O_2] + k_2[Sub]} \quad (2)$$

TABLE 3

Rate Constants (M$^{-1}$s$^{-1}$) for the [Fe$^{III}$(L2X)] (X = H, NO$_2$) IA, IB catalyzed bleaching of Orange II by [H$_2$O$_2$] at 25° C. in 0.01M Phosphate Buffer

| Catalyst | pH | $k_1$ [M$^{-1}$s$^{-1}$] | $k_2$ [M$^{-1}$s$^{-1}$] |
|---|---|---|---|
| 1A | 7.0 | (2.0 ± 0.1) × 10$^2$ | (2.0 ± 0.1) × 10$^4$ |
|  | 9.4 | (2.8 ± 0.2) × 10$^3$ | (1.12 ± 0.10) × 10$^5$ |
|  | 11.0 | (3.4 ± 0.2) × 10$^4$ | (1.60 ± 0.10) × 10$^5$ |
| 1B | 7.0 | (1.24 ± 0.10) × 10$^3$ | (4.1 ± 0.5) × 10$^3$ |
|  | 9.4 | (2.36 ± 0.6) × 10$^3$ | (4.2 ± 0.4) × 10$^5$ |
|  | 11.0 | (2.4 ± 0.2) × 10$^4$ | (4.9 ± 0.5) × 10$^5$ |
| II | 11.0* | 3.5 × 10$^3$ | 1.50 × 10$^4$ |

*II shows maximum activity at pH 11.0 c. Kinetics of IB Catalyzed Bleaching of Safranine O by H$_2$O$_2$

Figure 13:
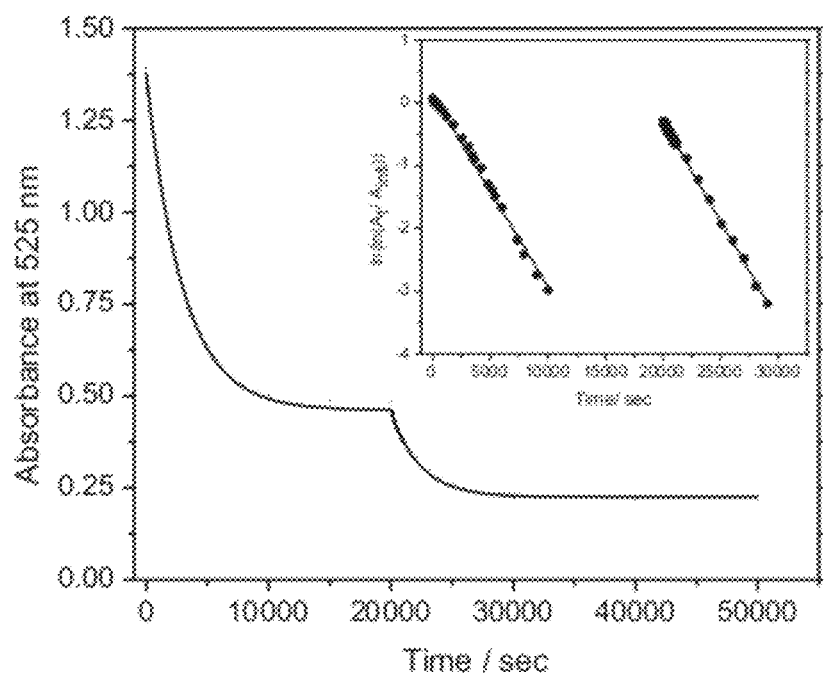
FIG. 13 depicts Kinetics of 1B catalyzed bleaching of Safranine O (4.22×10$^{-5}$ M) by H$_2$O$_2$ (0.012M). Initial concentration of 1B=7.5×10$^{-8}$ M at 25° C. in 0.01 M Phosphate Buffer; aliquots of the same amount of 1B were added after 20,000 sec to restart the reaction again. Inset figure shows linearization of the data obtained after each addition of 1B according to Equation (5).
Figure 14:
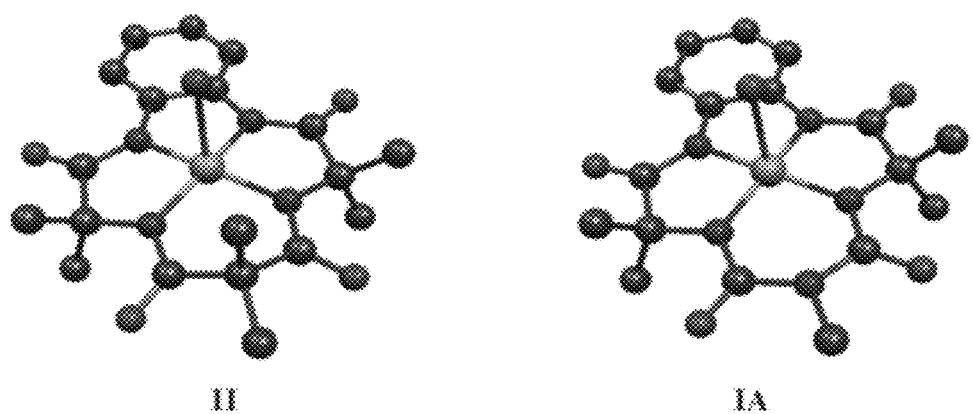
FIG. 14 depicts typical crystal structures of II (left) and IA (right)
Figure 15:
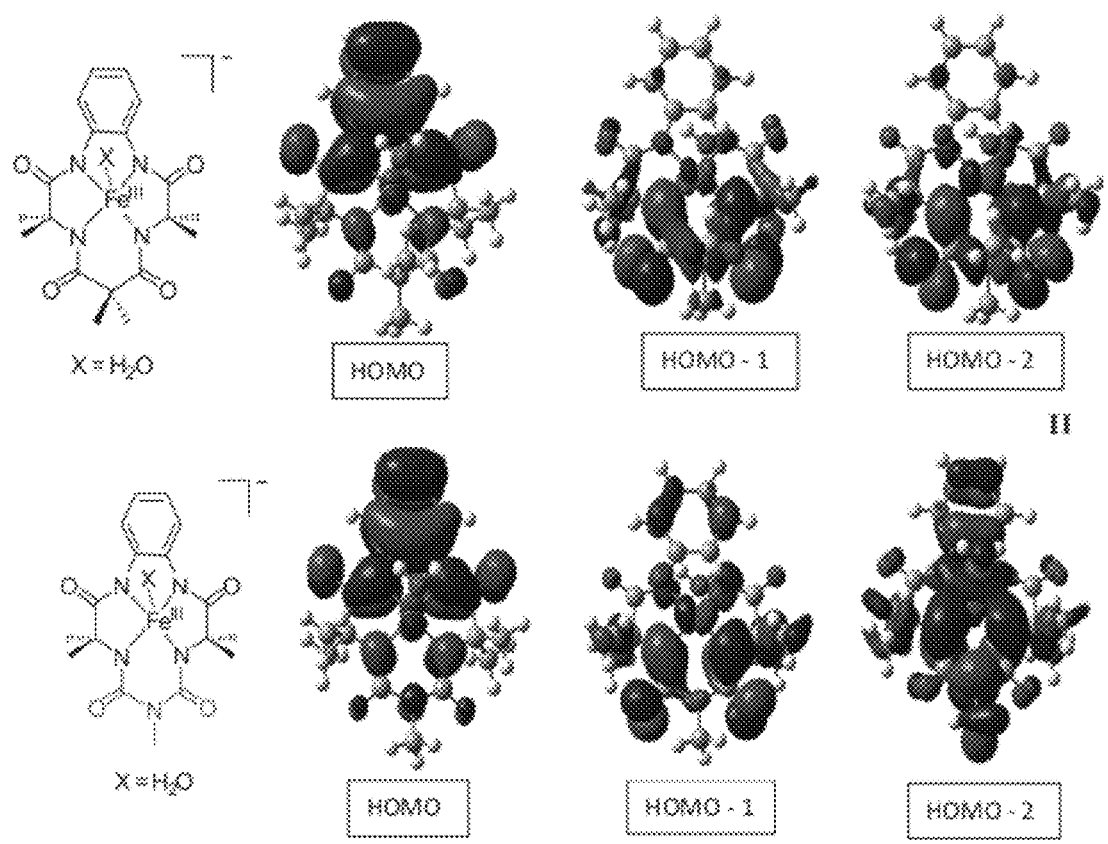
FIG. 15 depicts Frontier molecular orbitals: HOMO, HOMO-1 and HOMO-2 of II (upper) and 1A.
Figure 16:
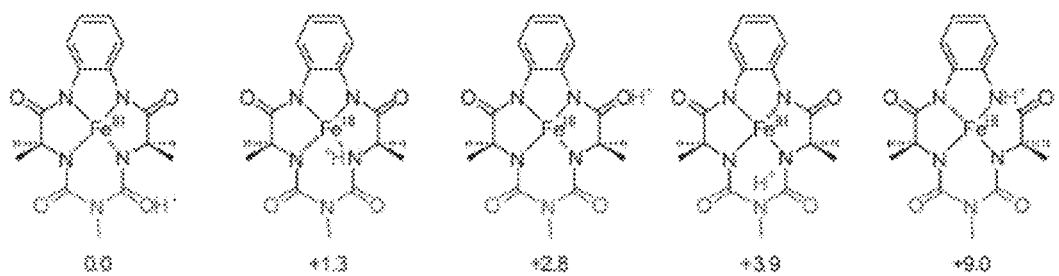
FIG. 16 depicts possible protonated species of IA in acidic media and their relative energies in the unit of kcal/mole, axial water is not shown for clarity.
Figure 17:
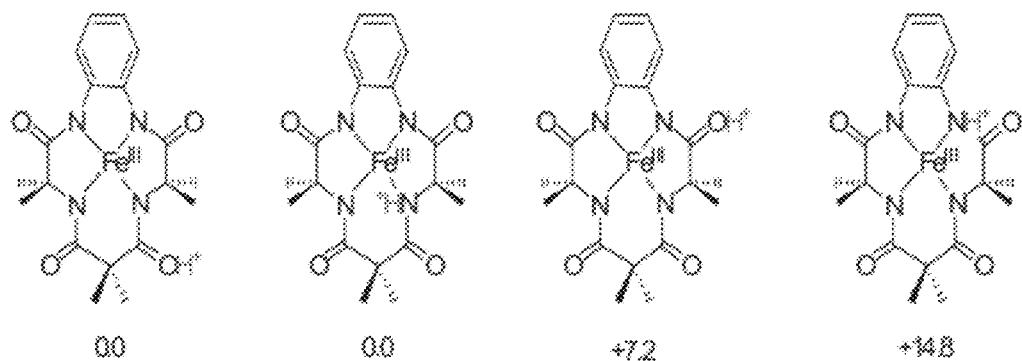
FIG. 17 depicts possible protonated species of II in acidic media and their relative energies in the unit of kcal/mole, axial water is not shown for clarity.

In FIG. 13 incomplete bleaching of safranine O is described even if [H$_2$O$_2$]>>>[dye]. Addition of second aliquot of H$_2$O$_2$ does not restart the catalytical bleaching after 20,000 sec of first cycle but addition of a new aliquot of catalyst brings back the reaction again, suggesting the complete deactivation of the catalyst after end of first cycle. To hold this condition the half-life as determined by k$_1$ or k$_{2i}$ should be greater than the time required for very large number catalytic turnovers as decided by k$_2$.

Kinetic analysis showed initial rate is directly proportional to [safranine O] and independent of [H$_2$O$_2$]i.e zero order with respect to [H$_2$O$_2$] which proves that the reaction holds k$_1$[H$_2$O$_2$]>k$_2$[safranine O] as well as k$_{-1}$ is negligible compared to the k$_1$[H$_2$O$_2$]. Compared to Orange II bleaching k$_2$ was significantly low for Safranine O at pH 11, which favors to hold the condition k$_1$[H$_2$O$_2$]>>k$_2$ [Safranine O] at pH 11.0 which suggests why safranine O bleaching is difficult for [FeIII(biuret-amide)](X=H, NO2) and safranine O is a perfect choice for determining intramolecular inactivation. For safranine O bleaching, Equation (2) can be simplified to Equation (3) and k$_2$ value can be calculated from the initial rate vs, [Safranine O] data as given in Table 4.

$$\frac{d[Sub]}{dt} = k_2[Fe^{III}]_{total}[Sub] \quad (2)$$

d. Intramolecular Inactivation (ki) Measurement for Safranine O Bleaching at pH 11.0

The mono exponential intramolecular inactivation rate constant (k$_i$) measurement of the oxidized form of the catalyst was done by the method followed by Collins group. The simplified differential rate law for dye bleaching is given by Equation (3) where D$_t$ and x are total concentrations of the dye and concentration of the bleached dye at time t respectively. Integrating the Equation (3) under the boundary condition x=x∞ at t=t∞ results Equation (4). Equation (5) was derived by replacing the concentration terms by the absorbance term.

$$\frac{d(D_t - x)}{dt} = k_2(D_t - x)([Fe^{III}]_{total}e^{-k_i t}) \quad (3)$$

$$\ln\left[\ln\left(\frac{D_t - x}{D_t - x_\alpha}\right)\right] = \ln\left(\frac{k_2}{k_i}[Fe^{III}]_{total}\right) - k_i t \quad (4)$$

$$\ln\left[\ln\left(\frac{A_t}{A_\alpha}\right)\right] = \ln\left(\frac{k_2}{k_i}[Fe^{III}]_{total}\right) - k_i t \quad (5)$$

From the slope of the double logarithm of the ratio A$_t$/A$_\infty$ vs. time plot in Equation 6 gives the value of ki (FIG. 13, Table 4). The rate constant k$_2$ is calculated from the intercept of the plot by putting the value of k$_i$.

TABLE 4

Rate Constants k$_i$ (s$^{-1}$) and k$_2$ (M$^{-1}$s$^{-1}$) of IA, IB catalysis in comparison with II in terms of Safranine O bleaching by H$_2$O$_2$ at pH 11.0, 25° C.

| Catalyst | $k_i \times 10^4$ [s$^{-1}$] | $k_2 \times 10^{-3}$ [M$^{-1}$s$^{-1}$]$^a$ | $k_2 \times 10^{-3}$ [M$^{-1}$s$^{-1}$]$^b$ |
|---|---|---|---|
| 1A | 3.7 ± 0.1 | 2.0 ± 0.1 | 2.4 ± 0.1 |
| 1B | 3.0 ± 0.2 | 3.8 ± 0.3 | 3.9 ± 0.1 |
| II | 34 ± 3 | 11.0 ± 1.0 | 12.0 ± 1.0 |
| II (CF$_2$) | 130 ± 10 | 100 ± 20 | |

$^a$from Equation (5);
$^b$from initial rates

Figure 22:
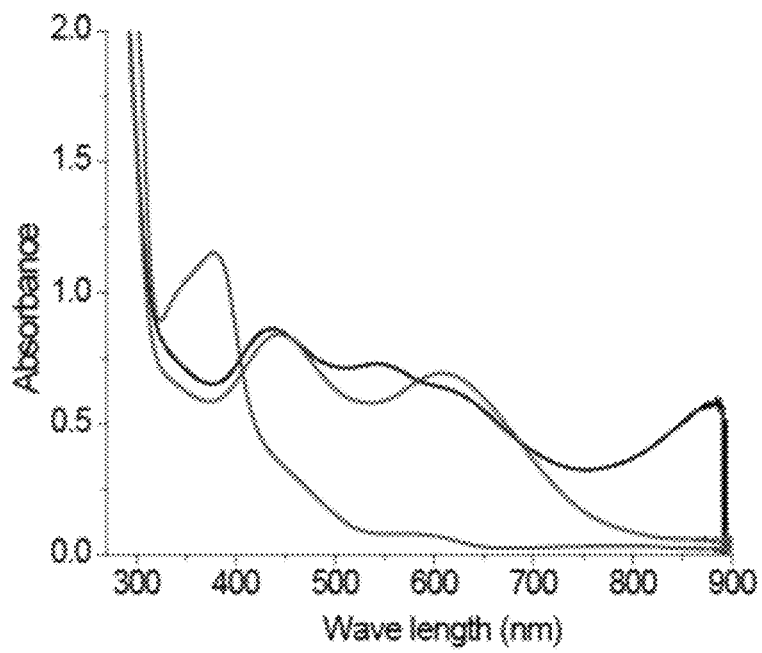
FIG. 22 depicts electronic absorption spectra of [Fe$^{III}$(biuret-amide)] (blue) before addition of mCPBA, mixture of Fe$^{IV}$-oxo and Fe$^{V}$-oxo (black) just after addition of mCPBA and Fe$^{V}$-oxo after 40 seconds (red).
Figure 23:
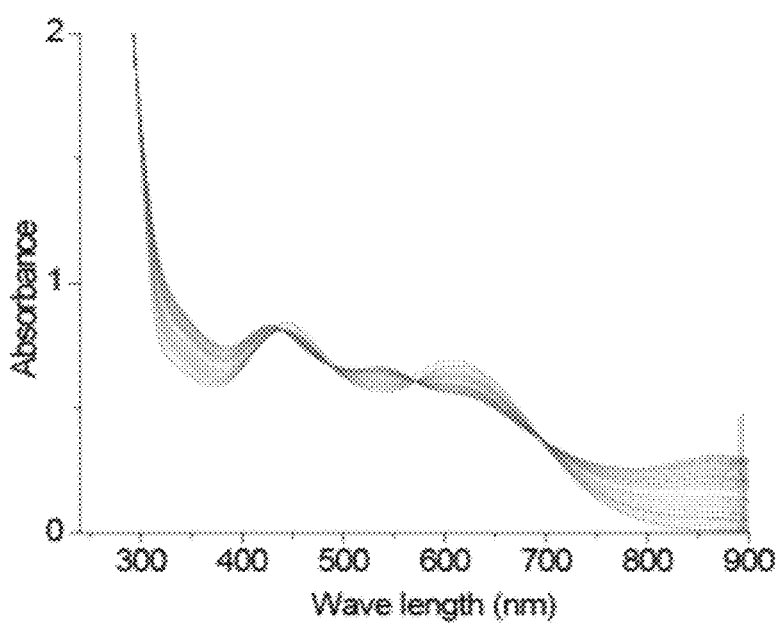
FIG. 23 depicts electronic spectra which shows that Fe$^{V}$-oxo peak is diminishing over 30 minutes and generation of Fe$^{IV}$-oxo peak.

[IV]. Spectroscopic Evidence for Fe(V)-Oxo Complex and its Reactivity Towards Unactivated C—H Bond at Room Temperature a. Generation of Fe$^V$-Oxo Complex In to a 4×10$^{-4}$ M solution of [Fe$^{III}$(biuret-amide] in acetonitrile 1 equivalent of mCPBA was added at room temperature to form a green colored solution followed by a purple color. The purple color indicates a $Fe^{IV}$-oxo species and the green a $Fe^V$-oxo species (FIG. 22). The characteristic band for $Fe^V$-oxo species at 440 nm and 630 nm reached a maximum just after addition and stayed intact for a period of 30 minutes (FIG. 23) that is enough for a typical C—H bond activation.

b. Oxidation of Cyclohexane

Figure 24:
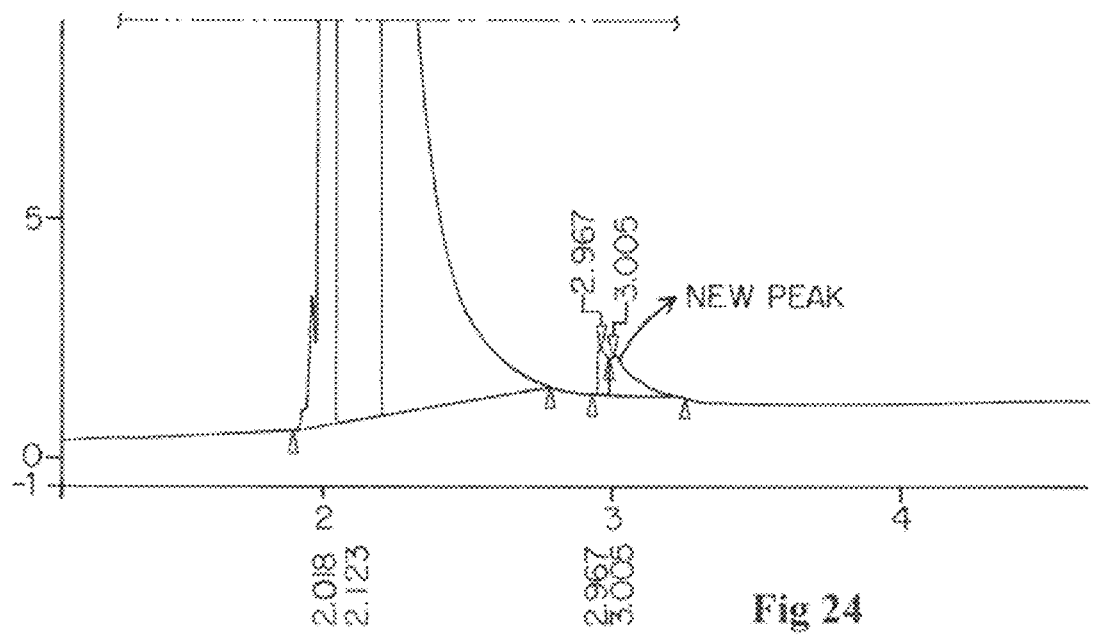
FIG. 24 depicts new Peak of cyclohexanone (3.005 min) and cyclohexanol (2.967 min) that were generated (solvent Ethyl acetate).

After the formation of $Fe^V$-oxo complex excess cyclohexane was added to it and the green colour of $Fe^V$-oxo was disappeared in 20 min. To isolate the organic products from the mixture containing metal complex, the solution was filtered over silica gel with ethyl acetate. The solution was then analyzed by GC (FIG. 24)

c. Oxidation of Toluene

Figure 25:
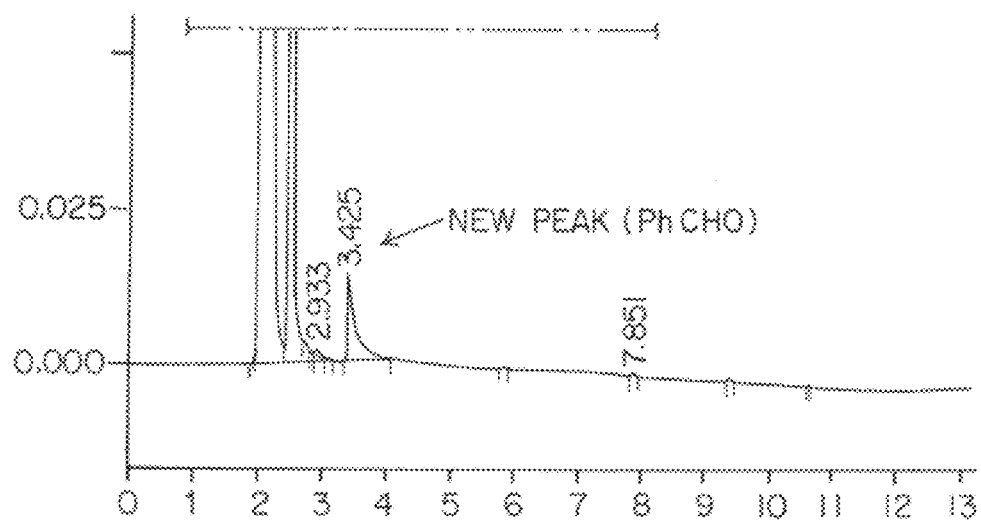
FIG. 25 depicts benzaldehyde (3.425 min) peak which was generated.
Figure 26:
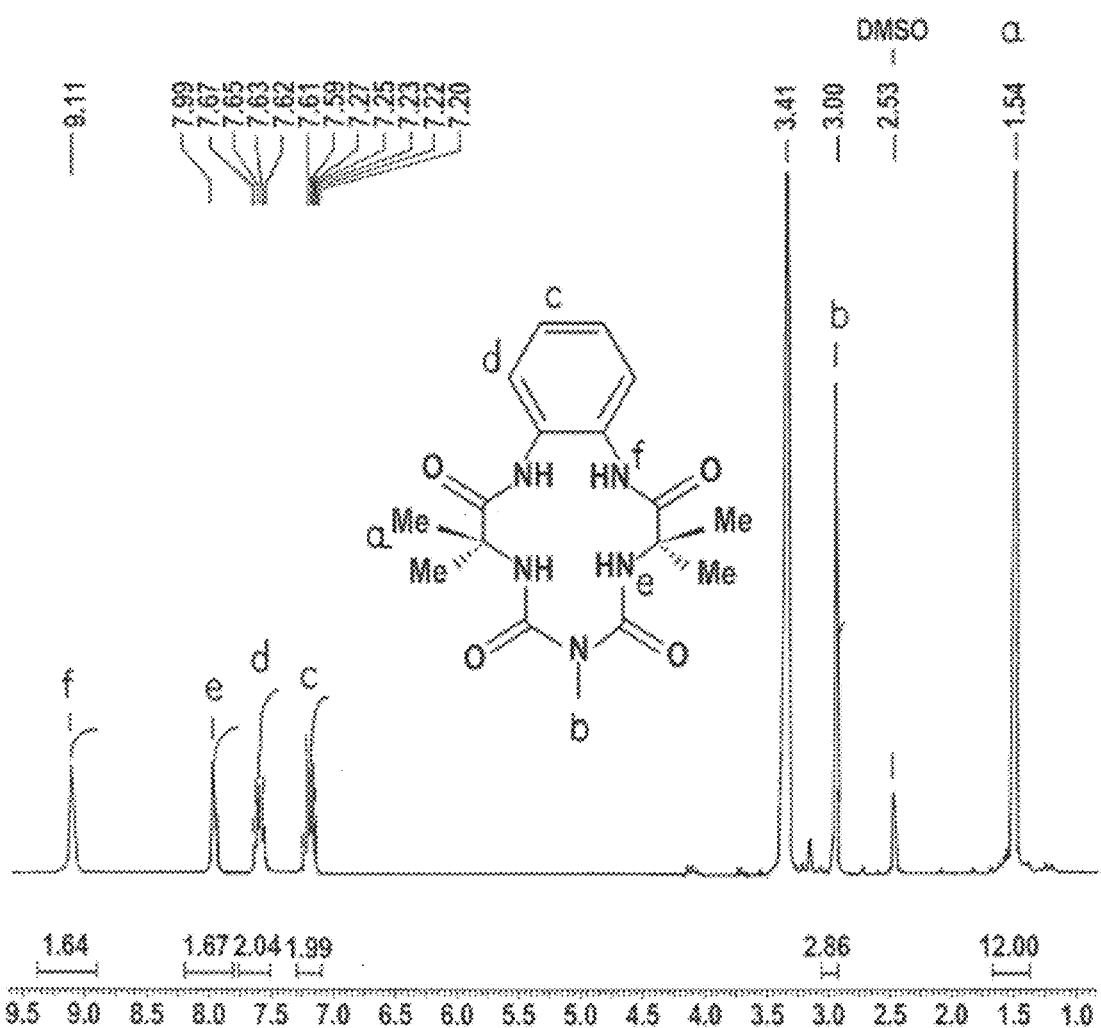

Same procedure was followed for toluene oxidation and the solution was then analyzed by GC (FIG. 25).

INDUSTRIAL ADVANTAGES OF THE INVENTION

By installing a substituted biuret moiety onto the ligand framework, the current inventors have synthesized a new generation of macrocyclic metal (III) complex that exhibit both excellent reactivity and stability, especially at low pH and high ionic strength.

Further, the catalyst comprises of elements that are truly biocompatible which makes it a suitable candidate for environmental remediation.

The current invention has demonstrated that the deprotonated Me-substituted biurets can be excellent ligands for the designing of functional peroxidase mimics.

The incorporation of electron withdrawing groups at the head aromatic ring tames down the oxidative degradation and gives extra stability in strongly acidic medium.

The present invention has achieved a new generation of macrocyclic metal (III) complex that exhibit both excellent reactivity and stability, especially at low pH and high ionic strength without introducing non-ecofriendly electronegative fluorine with overall improved performance compared to normal Fe-TAML in view of green oxidation.

We claim:

1. A biocompatible metal complex of a biuret-amide based macrocyclic ligand of Formula X $[M^{III}L_1].P$            Formula X, wherein M is a metal selected from the group consisting of Cr, Mn, Fe, Cu, Ni and Co;

L1 is a biuret-amide based macrocyclic ligand;

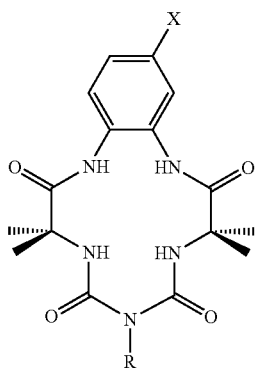

L1 wherein X=hydrogen, or electron withdrawing groups selected from the group consisting of —$NO_2$, —COOH, —COOR, —COCl or —CN; and R=C1-C3 alkyl or phenyl which may be optionally substituted; and P represents a cation selected from $Li^+$ or $Et_4N^+$.

2. The biocompatible metal (III) complex according to claim 1, wherein M is Fe and the complex has Formula Y:

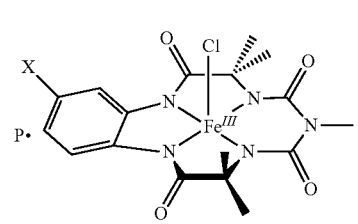

Formula Y wherein X=hydrogen, or electron withdrawing groups selected from the group consisting of —$NO_2$, —COOH, —COOR, —COCl or —CN; and P represents a cation selected from $Li^+$ or $Et_4N^+$.

3. The biocompatible metal complex according to claim 1, wherein the biuret-amide based macrocyclic ligand L1 has chemical structure L1a or L1b:

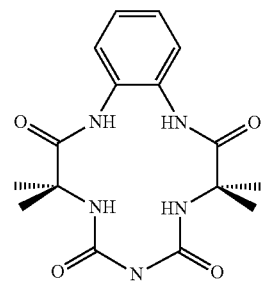

L1a

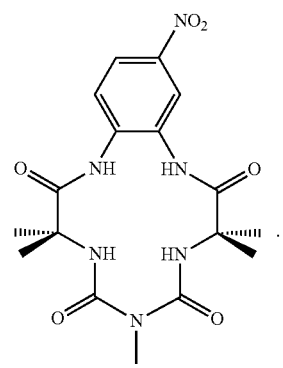

L1b

4. The biocompatible metal complex of a biuret-amide based macrocyclic ligand of Formula X according to claim 1, wherein the metal complex is useful for $H_2O_2$ oxidation of a wide spectrum of targets selected from the group consisting of toxic polychlorophenols, thiophosphate pesticides, nitrophenols, azo dyes, dibenzothiophenes, anthrax surrogates, and natural and synthetic estrogens, in effluent bleaching, in synthesis of small molecules selected from the group consisting of N-oxides, epoxides and aldehydesby oxidation, and as functioning analogues of catalase-peroxidase enzymes.

5. The biocompatible metal complex of a biuret-amide based macrocyclic ligand of Formula X according to claim 1, wherein the metal complex exhibits reactivity for the activation of $H_2O_2$, and stability at pH in the range of 2 to 5 and ionic strength up to 0.5M.

6. A process for synthesis of a compound according to claim 1,
the process comprising the steps of:
a. mixing a diamine of Formula 1 in Tetrahydrofurane (THF) and base to obtain a mixture;

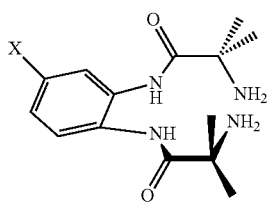

1 wherein X=hydrogen, or electron withdrawing groups selected from the group consisting of —$NO_2$, —COOH, —COOR, —COCl or —CN;
b. adding a N,N-dichloroformyl (aryl/alkyl)amine of Formula 2 dissolved in dry THF in the mixture as obtained in step (a) at 0° C. under nitrogen for a period in the range of 50 to 70 minutes to obtain a solution;

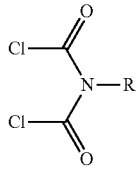

2 wherein R=C1-C3 alkyl or phenyl which may be optionally substituted;
c. allowing the solution as obtained in step (b) to warm to temperature in the range of 25 to 35° C., stirring for 11 to 13 hours to obtain the macrocylic ligand of Formula L1;

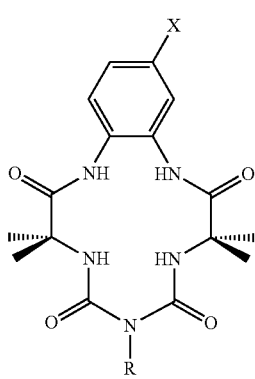

L1 wherein X=hydrogen, or electron withdrawing groups selected from the group consisting of —$NO_2$, —COOH, —COOR, —COCl or —CN, and R=C1-C3 alkyl or phenyl which may be optionally substituted; and
d. inserting the metal M, where M is a metal selected from the group consisting of Cr, Mn, Fe, Cu, Ni and Co, using a metal precursor, into the ligand of Formula L1 in presence of a base and a non-polar solvent followed by addition of a cationic salt by a process known in the art.

7. The process according to claim 6, wherein the base used in step (a) is selected from diethylamine or triethylamine.

8. The process according to claim 6, wherein the cation used in step (d) is selected from $[Et_4N]^+$ or $Li^+$.

9. A process for synthesis of a compound according to claim 3 comprising the steps of:
a. cyclizing a diamine of Formula 1

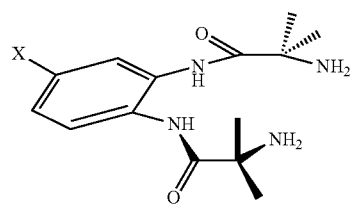

1 with N,N-dichloroformyl (aryl/alkyl)amine of Formula 2

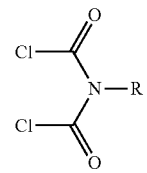

2 dissolved in dry THF, base and chloroform at 0° C. under nitrogen, allowing to warm at temperature in the range of 25 to 35° C., stirring for about 12 hours to obtain the macrocylic ligand of Formula L1; and
b. inserting Fe (III) chloride into the biuret-amide ligand of Formula L1a using $FeCl_2$ in presence of a base n-butyl lithium and non-polar solvent followed by addition of $Et_4N^+$ by a process known in the art.

10. The biocompatible metal complex according to claim 2, wherein the complex has Formula YL1a:

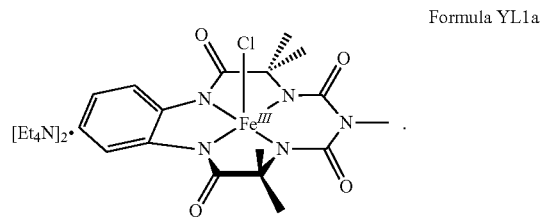

Formula YL1a

11. The biocompatible metal complex according to claim 2, wherein Formula X is $(Et_4N).[Fe^{III}$ biuret-amide$)]$.

12. The biocompatible metal complex according to claim 2, wherein the complex is Tetraethyl ammonium 3,3,6,9,9-pentamethyl-1,4,8,11-tetrahydro-1H-benzo[i][1,4,6,8,11] pentaazacyclotridecine-2,5,7,10(6H,11H)-tetraone ferrate.

13. The biocompatible metal complex according to claim 2, wherein the complex has Formula YL1b:
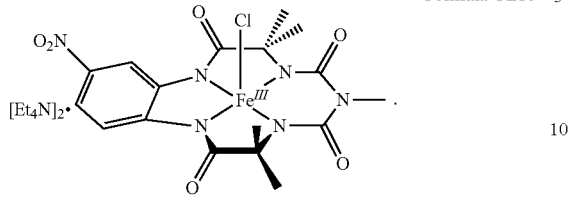
Formula YL1b